United States Patent [19]

Kawashima et al.

[11] Patent Number: 5,968,980
[45] Date of Patent: Oct. 19, 1999

[54] 1,3-DIALKYLUREA DERIVATIVE

[75] Inventors: Yoichi Kawashima, Kyoto; Ken-ichi Fujimura, Higashiosaka; Hiroshi Suhara, Osaka; Noriyoshi Yamamoto, Shijonawate; Hiromi Matsumoto, Osaka; Nobuaki Miyawaki, Sanda; Yuko Fujita, Osaka, all of Japan

[73] Assignee: Santen Pharmaceutical Co., Ltd., Osaka, Japan

[21] Appl. No.: 08/849,402

[22] PCT Filed: Dec. 19, 1995

[86] PCT No.: PCT/JP95/02539

§ 371 Date: Jun. 3, 1997

§ 102(e) Date: Jun. 3, 1997

[87] PCT Pub. No.: WO96/18606

PCT Pub. Date: Jun. 20, 1996

[30] Foreign Application Priority Data

Dec. 14, 1994 [JP] Japan ................................. 6-310493

[51] Int. Cl.⁶ ...................... C07C 275/18; A61K 31/215
[52] U.S. Cl. ......................... 514/534; 514/566; 560/34; 562/439
[58] Field of Search ................ 560/34; 562/439; 514/534, 566

[56] References Cited

U.S. PATENT DOCUMENTS

| | | |
|---|---|---|
| 4,028,401 | 6/1977 | Fessler et al. . |
| 4,515,803 | 5/1985 | Henning et al. . |
| 4,624,962 | 11/1986 | Henning et al. . |
| 4,728,620 | 3/1988 | Haslanger et al. . |
| 5,066,658 | 11/1991 | Demers et al. . |
| 5,140,009 | 8/1992 | Haviv et al. . |
| 5,175,183 | 12/1992 | Brooks et al. . |
| 5,262,178 | 11/1993 | Malfroy-Camine et al. . |
| 5,403,585 | 4/1995 | Malfroy-Camine et al. . |

FOREIGN PATENT DOCUMENTS

| | | |
|---|---|---|
| 54862 | 6/1982 | European Pat. Off. . |
| 53-5119 | 1/1978 | Japan . |
| 58-55451 | 4/1983 | Japan . |
| 61-40252 | 2/1986 | Japan . |
| 62-294650 | 12/1987 | Japan . |
| 3-81292 | 4/1991 | Japan . |
| 3-79339 | 12/1991 | Japan . |
| 4-503074 | 6/1992 | Japan . |
| 6-72985 | 3/1994 | Japan . |
| 6-184086 | 7/1994 | Japan . |

OTHER PUBLICATIONS

M.A. Fitzpatrick J.J. Rademaker, C.J. Charles, T.G. Yandle, E.A. Espiner, H. Ikam and C. Sybetz, Acute Hemodynamic, Hormonal, and Renal Effects of Neutral Endopeptidase Inhibition in Ovine Heart Failure, *Journal of Cardiovascular Pharmacology*, 19, 635–640 (1992).

Andrea A. Seymour, Magdi M. Asaad, Vita M. Lanoce, Kathleen M. Langenbacher, Susan A. Fennel, "Systemic Hemodynamics, Renal Function and Hormonal Levels During Inhibition of Neutral Endopeptidase 3.4.24.11 and Angiotensin–Converting Enzyme in Conscious Dogs With Pacing–Induced Heart Failure", *The Journal of Pharmacology and Experimental Therapeutics*, 266, 872–883 (1993).

(List continued on next page.)

*Primary Examiner*—Robert Gerstl
*Attorney, Agent, or Firm*—Frishauf, Holtz, Goodman, Langer & Chick, P.C.

[57] ABSTRACT

The present invention relates to compounds represented by the formula [I] and salts thereof, wherein $R^1$ and $R^5$ each represents carboxyl, phosphonic or a derivative thereof; $R^2$ represents hydrogen, lower alkyl, (substituted) phenyl lower alkyl, lower alkoxy or (substituted) phenyl lower alkoxy; $R^3$ represents lower alkyl or (substituted) phenyl lower alkyl; and $R^4$ represents a group represented by the formula [XI], [XII] or [XIII]. The compounds of the present invention have endopeptidase 24.11 inhibitory activity and are useful for treating cardiovascular diseases such as heart failure and hypertension, renal diseases such as renal failure, gastroenteric disorders such as diarrhea and hyperchlorhydria, endocrine and metabolic diseases such as obesity, and autoimmune diseases such as rheumatic disease, and for mitigating myosalgia, migraine, etc.

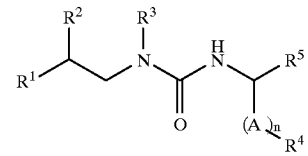

[I]

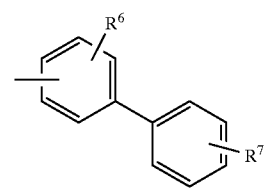

[XI]

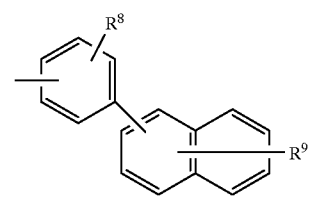

[XII]

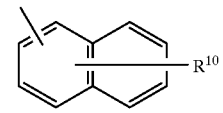

[XIII]

40 Claims, No Drawings

OTHER PUBLICATIONS

I. Pham, W. Gonzalez, A.-I.K. El Amrani, M.-C. Fournié, M. Philippe, I. Laboulandine, B.P. Roques and J.-B. Michel, "Effects of Converting Enzyme Inhibitor and Neural Endopeptidase Inhibitor on Blood Pressure and Renal Function in Experimental Hypertension", *The Journal of Pharmacology and Experimental Therapeutics*, 265, 1339–1347 (1993).

Helen M. Lafferty, Mark Gunning, Patricio Silva, Mark B. Zimmerman, Barry M. Brenner and Sharon Anderson, "Enkephalinase Inhibition Increases Plasma Atrial Natriuretic Peptide Levels, Glomerular Filtration Rate, and Urinary Sodium Excretion in Rats With Reduced Renal Mass", *Circulation Research*, 65, 640–646 (1989).

Maria Chicau–Chovet, Marcelle Dubrasquet, Jacques Chariot, Annick Tsocas Jeanne–Marie Lecomte and Claude Rozé, "Thiorphan and acetorphan inhibit gastric secretion by a central, non–opioid mechanism in the rat", *European Journal of Pharmacology*, 154, 247–254 (1988).

Ph. Baumer, E. Danquechin Dorval, J. Bertrand, J.M. Vetel, J.C. Schwartz, J.M. Lecomte, "Effects of acetorphan, an enkephalinase inhibitor, on experimental and acute diarrhoea", *Gut*, 33, 753–758 (1992).

Margaret A. Shipp, George E. Tarr, Chang–Yan Chen, Stephanie N. Switzer, Louis B. Hersh, Harald Stein, Mary E. Sunday and Ellis L. Reinherz, "CD10/neutral endopeptidase 24.11 hydrolyzes bombesin–like peptides and regulates the growth of small cell carcinomas of the lung", *Proc. Natl. Acad. Sci. USA*, 88, 10662–10666 (1991).

B.P. Roques, M.C. Fournié–Zaluski, E. Soroca, J.M. Lecomte, B. Malfroy, C. Llorens and J.–C. Schwartz, "The enkephalinase inhibitor thiorphan shows antinociceptive activity in mice", *Nature*, 286–288 (1980).

R.J. Lieverse, J.B.M.F. Jansen, A. van de Zwan, L. Samson, A.A.M. Masclee, L.C. Rovati and C.B.H.W. Lamers, "Bombesin Reduces Food Intake in Lean Man by a Cholecystokinin–Independent Mechanism", *Journal of Chemical Endocrinology and Metabolism*, 76, 1495–1498 (1993).

M. Matucci–Cerinic, A. Lombardi, G. Leoncini, A. Pignone, L. Sacerdoti, M.G. Spillantini and G. Partsch, "Neutral endopeptidase (3.4.24.11) in plasma and synovial fluid of patients with rheumatoid arthritis. A marker of disease activity or a regulator of pain and inflammation?", *Rheumatol Int*, 13, 1–4 (1993).

# 1,3-DIALKYLUREA DERIVATIVE

TECHNICAL FIELD

The present invention relates to a novel 1,3-dialkylurea derivative which has inhibitory effects on endopeptidase 24.11 and is useful as a therapeutic agent for cardiovascular diseases such as heart failure and hypertension, renal diseases such as renal failure, gastroenteric disorders such as diarrhea and hyperchlorhydria, endocrine and metabolic diseases such as obesity, and autoimmune diseases such as rheumatic disease, and as analgestics for myosalgia, migraine, etc. The novel 1,3-dialkylurea derivative has a group wherein a plurality of aromatic monocyclic hydrocarbons are combined or condensed, such as a biphenylyl group and a naphthyl group, and has carboxyl group(s) and/or phosphonic group(s) which are introduced into each terminal end of both alkylene chains.

BACKGROUND ART

Endopeptidase 24.11, which is one of neutral endopeptidases, is a metal-containing neutral peptidase which is required to contain zinc in its active center and it is also called enkephalinase or an antigen of acute lymphoblast leukemia (CD10).

Endopeptidase 24.11 is an enzyme which distributes widely, for example, in the kidney, lungs, central nervous system, the intestinal canal, neutrophil, fibroblast, vascular endothelial cells, etc. and hydrolyzes various physiologically active peptides such as artial natriuretic polypeptide (ANP), enkephaline, bradykinin and substance P. Accordingly, the enzyme is known to take part in various biofunctions and to exhibit various therapeutic effects by inhibiting the above-mentioned enzymatic activity.

These effects are exemplified by an effect on cardiovascular diseases such as heart failure indicating symptoms of edema and hypertension, an effect on renal diseases such as renal failure indicating symptom of edema or an increase of ascites, an effect on gastroenteric disorders such as diarrhea and hyperchlorhydria, an analgestic effect, an effect on endocrine and metabolic diseases such as obesity, and an effect on autoimmune diseases such as rheumatic disease.

Substances inhibiting endopeptidase 24.11 are described below in more detail.

The following effects of compounds inhibiting endopeptidase 24.11 have been observed. An increasing effect of total urine volume and urinary sodium excretion has been observed on heart failure models by rapid ventricular pacing method (J. Cardiovasc. Pharmacol., 19, 635–640 (1992)). An increasing effect of urinary ANP excretion and urinary cyclic GMP excretion has been observed (J. Pharmacol. Exp. Ther., 266, 872–883 (1993)). A hypotensive effect has been observed using spontaneously hypertensive rats or deoxycorticosteron acetate induced hypertensive rats (J. Pharmacol. Exp. Ther., 265, 1339–1347 (1993)). An increasing effect of urinary sodium excretion has been observed using rats subjected to five-sixths renal ablation (Circ. Res., 65, 640–646 (1989)). An inhibitory effect, which is derived from the effect on the central nervous system, upon pentagastrin-stimulated gastric secretion has been observed (Eur. J. Pharmacol., 154, 247–254 (1988)). An improvement effect of acute diarrhea caused by castor oil has been observed (Gut, 33, 753–758 (1992)). An analgestic effect has been observed by the tail-withdrawal test and the hotplate jump test (Nature, 288, 286–288 (1980)). In addition, since bonbesin (Proc. Natl. Acad. Sci., 88, 10662–10666 (1991)), which is known as one of substrates of endopeptidase 24.11, has been reported to reduce food intake (J. Clin. Endocrinol. Metab., 76, 1495–1498 (1993)), a compound inhibiting endopeptidase 24.11 is expected to be a therapeutic agent for endocrine and metabolic disease such as obesity. Since an endopeptidase 24.11 activity in blood and synovial fluid has been reported to be higher in patients with rheumatoid arthritis than in healthy men and patients with osteoarthritis (Rheumatol. Int., 13,1–4 (1993)), a compound inhibiting endopeptidase 24.11 is expected to be a therapeutic agent for autoimmune disease where an immune function is lowered such as rheumatic disease.

On the other hand, a structural feature of the present invention is that carboxyl group(s) and/or phosphonic group (s) are introduced into each terminal end of both alkylene chains of 1,3-dialkylurea and further a group wherein a plurality of aromatic monocyclic hydrocarbons are combined or condensed, such as biphenylyl group and naphthyl group is introduced into the alkylene chains. Prior art is described below from the standpoint of the chemical structure.

It has been reported that 1,3-dialkylurea derivatives wherein a carboxyl group is introduced at the end of one alkylene chain have angiotensin II antagonistic effect (Laid-open Japanese Patent Publication Nos. 6-72985 and 6-184086). It has been reported that 1,3-dialkylurea derivatives wherein carboxyl groups are introduced at the ends of both alkylene chains inhibit an angiotensin-converting enzyme (Laid-open Japanese Patent Publication No. 58-55451). It has also been reported that amino acid derivatives containing a nitrogen atom located at the 3rd position of 1-(carboxyalkylamino)urea derivatives inhibit an activity of enkephalinase (Examined Japanese Patent Publication No. 3-79339). However, none of them disclose a compound wherein a biphenyl group or a naphthyl group is introduced into an alkylene chain of a 1,3-dialkylurea derivative.

It is reported that an alkylurea derivative containing a biphenylyl group or a naphthyl group can be used as an agent for inhibiting allergy (Laid-open Japanese Patent Publication No. 62-294650) and a bronchodilator (U.S. Pat. No. 5,066,658). It is also reported that a compound wherein a terminal end of an alkylene chain is a hydroxamic group inhibits biosynthesis of leukotriene because it has a lipoxygenase inhibition activity (WO90/08545). It is also reported that an analogue of a luteinizing hormone releasing hormone controls a level of a sex hormone (Laid-open Japanese Patent Publication No. 3-81292). However, none of them disclose a compound wherein carboxyl group(s) and/or phosphonic group(s) are introduced into each terminal end of both alkylene chains of a 1,3-dialkylurea derivative having a biphenylyl group or a naphthyl group.

As mentioned above, various studies have been made for the 1,3-dialkylurea derivatives, but there has never been studied about an urea derivative wherein carboxyl group(s) and/or phosphonic group(s) are introduced into each terminal end of both alkylene chains and, furthermore, a group wherein a plurality of aromatic monocyclic hydrocarbons are combined or condensed is introduced into one alkylene group. It was a very interesting subject to synthesize such compounds and to examine their pharmacological effects, particularly their effects on endopeptidase 24.11.

The present inventors have paid attention to the alkylene chains of the 1,3-dialkylurea derivative, synthesized a novel urea derivative wherein carboxyl group(s) and/or phosphonic group(s) are introduced into each terminal end of both alkylene chains and, furthermore, a group wherein a plurality of aromatic monocyclic hydrocarbons are combined or condensed is introduced into one alkylene group and then studied about the pharmacological effects thereof.

As a result of the study using N-dansyl-D-alanyl-glycyl-p-nitrophenylalanyl-glycine, which is known as a substrate of endopeptidase 24.11, it has been found that the novel urea derivatives wherein carboxyl group(s) and/or phosphonic group(s) are introduced into each terminal end of both alkylene chains and, furthermore, a group wherein a plurality of aromatic monocyclic hydrocarbons are combined or condensed is introduced into one alkylene group have high inhibitory activities to endopeptidase 24.11.

DISCLOSURE OF THE INVENTION

The present invention relates to a compound represented by the following general formula [I] and a salt thereof (hereinafter referred to as a "present compound").

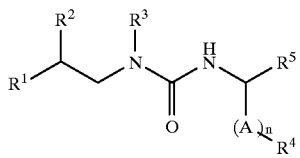

[I]

wherein $R^1$ represents a carboxyl group which can be converted into an ester, an amide or a hydroxamic acid, or a phosphonic group which can be converted into an ester;

$R^2$ represents a hydrogen atom, a lower alkyl group, a phenyl lower alkyl group, a lower alkoxy group or a phenyl lower alkoxy group, and each phenyl ring of the phenyl lower alkyl group and the phenyl lower alkoxy group can be substituted by a halogen atom, a lower alkyl group, a hydroxy group, a lower alkoxy group, a lower alkylenedioxy group, a nitro group, an amino group or a lower alkylamino group;

$R^3$ represents a lower alkyl group or a phenyl lower alkyl group, and the phenyl ring of the phenyl lower alkyl group can be substituted by a halogen atom, a lower alkyl group, a hydroxy group, a lower alkoxy group or a lower alkylenedioxy group;

$R^5$ represents a carboxyl group which can be converted into an ester, an amide or a hydroxamic acid, or a phosphonic group which can be converted into an ester;

$R^4$ represents a group represented by the following general formula [XI], [XII] or [XIII];

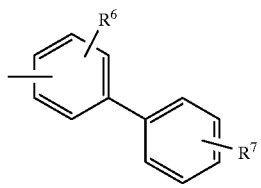

[XI]

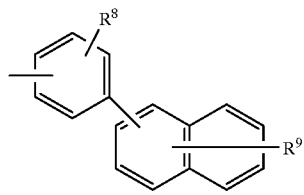

[XII]

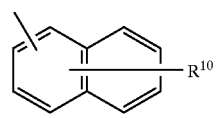

[XIII]

wherein
$R^6$ represents a hydrogen atom, a halogen atom, a lower alkyl group, a hydroxy group, a lower alkoxy group, a lower alkylenedioxy group, a nitro group, an amino group or a lower alkylamino group;

$R^7$ represents a hydrogen atom, a halogen atom, a lower alkyl group, a hydroxy group, a lower alkoxy group, a lower alkylenedioxy group, a nitro group, an amino group, a lower alkylamino group, a phenyl group which can be substituted by a substituent or a naphthyl group which can be substituted by a substituent, and the above substituent represents a halogen atom, a lower alkyl group, a hydroxy group, a lower alkoxy group, a lower alkylenedioxy group, a nitro group, an amino group or a lower alkylamino group;

$R^8$ represents a hydrogen atom, a halogen atom, a lower alkyl group, a hydroxy group, a lower alkoxy group, a lower alkylenedioxy group, a nitro group, an amino group or a lower alkylamino group;

$R^9$ represents a hydrogen atom, a halogen atom, a lower alkyl group, a hydroxy group, a lower alkoxy group, a lower alkylenedioxy group, a nitro group, an amino group, a lower alkylamino group, a phenyl group which can be substituted by a substituent or a naphthyl group which can be substituted by a substituent, and the above substituent represents a halogen atom, a lower alkyl group, a hydroxy group, a lower alkoxy group, a lower alkylenedioxy group, a nitro group, an amino group or a lower alkylamino group;

$R^{10}$ represents a hydrogen atom, a halogen atom, a lower alkyl group, a hydroxy group, a lower alkoxy group, a lower alkylenedioxy group, a nitro group, an amino group, a lower alkylamino group, a phenyl group which can be substituted by a substituent or a naphthyl group which can be substituted by a substituent, and the above substituent represents a halogen atom, a lower alkyl group, a hydroxy group, a lower alkoxy group, a lower alkylenedioxy group, a nitro group, an amino group or a lower alkylamino group;

"A" represents a lower alkylene group;

"n" represents 0 or 1.

The same shall be applied hereinafter.

The groups defined above will be described in detail.

Examples of the halogen atom include fluorine, chlorine, bromine and iodine. Examples of the lower alkyl include straight-chain or branched alkyl having 1 to 6 carbon atoms, such as methyl, ethyl, propyl, butyl, hexyl, isopropyl, isobutyl, isopentyl, tert-butyl or (dimethyl)ethyl. Examples of the lower alkoxy include straight-chain or branched alkoxy having 1 to 6 carbon atoms, such as methoxy, ethoxy, propoxy, butoxy, hexyloxy, isopropoxy or tert-butoxy. Examples of the lower alkylenedioxy include alkylenedioxy wherein a straight-chain or branched alkylene having 1 to 6 carbon atoms is present between two oxygen atoms, such as methylenedioxy, ethylenedioxy, (dimethyl)methylenedioxy or (diethyl)methylenedioxy.

Examples of the ester of carboxylic acid include those which are normally used as the ester of carboxylic acid, for example, lower alkyl ester such as methyl ester, ethyl ester, butyl ester, hexyl ester, isopropyl ester, isobutyl ester or tert-butyl ester; lower alkanoylamino-lower alkyl ester such as acetylaminomethyl ester, acetylaminoethyl ester, propionylaminomethyl ester or propionylaminoethyl ester; phenyl lower alkyl ester such as benzyl ester; phenyl lower alkyl ester such as benzyl ester; phenyl ester, methoxyphenyl ester, acetamidophenyl ester, indanyl ester and the like. Examples of the lower alkanoyl include straight-chain or branched alkanoyl having 2 to 6 carbon atoms, such as acetyl, propionyl, butyryl, valeryl, isobutyryl, isovaleryl or pivaloyl. Examples of the ester of phosphonic acid include those which are used as the ester of phosphonic acid, such as methyl ester, ethyl ester, hexyl ester, isopropyl ester or tert-butyl ester. Examples of the amide include those which are normally used as the amide of carboxylic acid, such as amide with ammonia, amide with a lower alkylamine (e.g. methylamine, dimethylamine, ethylamine, etc.) or amide with a phenyl lower alkylamine (e.g. benzylamine, etc.).

The salts of the present compound may be any pharmaceutically acceptable salt, and is not specifically limited. Examples thereof include a salt with an inorganic acid (e.g. hydrochloric acid, nitric acid, sulfuric acid, etc.), a salt with a alkaline metal or an alkaline earth metal (e.g. sodium, potassium, calcium, etc.), an ammonium salt, and a salt with an organic amine (e.g. diethylamine, triethanolamine, etc.).

By the way, in the compound used as a drug, for the purpose of promoting absorption and improving long activity in the living body and stabilizing in preparation, formation of a prodrug (e.g. esterification of a carboxylic acid) and a method of using the derivative thereof as a synthesis intermediate are used as production means. Accordingly, the carboxyl group can also be converted into the form of the ester or amide as a general-purpose derivative of the carboxylic acid in the present invention.

Among the present compounds, preferred examples include the followings.

Compound (a) of the above general formula [I] wherein $R^1$ and $R^5$ are the same or different and represent a carboxyl group which can be converted into a lower alkyl ester, a lower alkanoylamino-lower alkyl ester, a phenyl lower alkyl ester, a phenyl ester or an indanyl ester; a carboxyl group which can be converted into an amide with ammonia, a lower alkylamine or a phenyl lower alkylamine; a carboxyl group which can be converted into a hydroxamic acid; or a phosphonic group which can be converted into a lower alkyl ester; and each phenyl ring of the phenyl lower alkyl ester, the phenyl ester and the phenyl lower alkylamine can be substituted by a halogen atom, a lower alkyl group, a hydroxy group, a lower alkoxy group, a lower alkylenedioxy group, a nitro group, an amino group, a lower alkylamino group or a lower alkanoylamino group; $R^2$ represents a hydrogen atom, a lower alkyl group, a phenyl lower alkyl group, a lower alkoxy group or a phenyl lower alkoxy group, and each phenyl ring of the phenyl lower alkyl group and the phenyl lower alkoxy group can be substituted by a halogen atom, a lower alkyl group, a hydroxy group, a lower alkoxy group, a lower alkylenedioxy group, a nitro group, an amino group or a lower alkylamino group; $R^3$ represents a lower alkyl group or a phenyl lower alkyl group, and the phenyl ring of the phenyl lower alkyl group can be substituted by a halogen atom, a lower alkyl group, a hydroxy group, a lower alkoxy group or a lower alkylenedioxy group; $R^4$ represents a group represented by the above general formula [XI], [XII] or [XIII] (wherein $R^6$ and $R^8$ are the same or different and represent a hydrogen atom, a halogen atom, a lower alkyl group, a hydroxy group, a lower alkoxy group, a lower alkylenedioxy group, a nitro group, an amino group or a lower alkylamino group; $R^7$, $R^9$ and $R^{10}$ are the same or different and represent a hydrogen atom, a halogen atom, a lower alkyl group, a hydroxy group, a lower alkoxy group, a lower alkylenedioxy group, a nitro group, an amino group, a lower alkylamino group, a phenyl group which can be substituted by a substituent or a naphthyl group which can be substituted by a substituent, and the above substituent represents a halogen atom, a lower alkyl group, a hydroxy group, a lower alkoxy group, a lower alkylenedioxy group, a nitro group, an amino group or a lower alkylamino group); "A" represents a lower alkylene group; and "n" represents 0 or 1, and salts thereof.

Among those belonging to the compound (a) and salts thereof, the following compounds are particularly preferred.

A compound wherein, in the compound (a), $R^4$ represents a group represented by the above general formula [XI], [XII] or [XIII] (wherein $R^6$ represents a hydrogen atom or a nitro group; $R^7$ represents a hydrogen atom, a halogen atom, a lower alkyl group, a hydroxy group, a lower alkoxy group, a nitro group, an amino group or a phenyl group; $R^8$ and $R^9$ each represents a hydrogen atom; and $R^{10}$ represents a hydrogen atom, a halogen atom or a lower alkoxy group), and salts thereof.

A compound wherein, in the compound (a), $R^4$ represents a group represented by the above general formula [XI], [XII] or [XIII] (wherein $R^6$ represents a hydrogen atom or a nitro group; $R^7$ represents a hydrogen atom, a halogen atom, a lower alkyl group, a lower alkoxy group or a phenyl group; $R^8$ and $R^9$ each represents a hydrogen atom; and $R^{10}$ represents a hydrogen atom, a halogen atom or a lower alkoxy group), and salts thereof.

A compound wherein, in the compound (a), $R^4$ represents a biphenylyl group, a fluorobiphenylyl group, a chlorobiphenylyl group, methylbiphenylyl group, a methoxybiphenylyl group, a nitrobiphenylyl group, a terphenylyl group, a naphthylphenyl group, a naphthyl group, a bromonaphthyl group or a methoxynaphthyl group, and salts thereof.

A compound wherein, in the compound (a), $R^4$ represents a group represented by the above general formula [XI] or [XIII] (wherein $R^6$ represents a hydrogen atom; $R^7$ represents a hydrogen atom, a halogen atom, a lower alkoxy group or a phenyl group; and $R^{10}$ represents a hydrogen atom or a lower alkoxy group), and salts thereof.

A compound wherein, in the compound (a), $R^4$ represents a biphenylyl group, a fluorobiphenylyl group, a methoxybiphenylyl group, a terphenylyl group, a naphthyl group or a methoxynaphthyl group, and salts thereof.

A compound wherein, in the compound (a), $R^3$ represents a lower alkyl group, particularly an isobutyl group or a phenyl lower alkyl group, and salts thereof.

A compound wherein, in the compound (a), $R^2$ represents a hydrogen atom, a lower alkyl group, a phenyl lower alkyl group, a lower alkoxy group or a phenyl lower alkyl group, and salts thereof.

A compound wherein, in the compound (a), $R^2$ represents a hydrogen atom, an isopentyl group, a benzyl group, a phenethyl group, a phenylpropyl group, a phenylbutyl group or a benzyloxy group, and salts thereof.

A compound wherein, in the compound (a), $R^1$ represents a carboxyl group which can be converted into a lower alkyl ester, a lower alkanoylamino-lower alkyl ester, a phenyl lower alkyl ester, a lower alkoxyphenyl ester, a lower alkanoylaminophenyl ester or an indanyl ester; a carboxyl group which can be converted into an amide with ammonia; a carboxyl group which can be converted into a hydroxamic acid; or a phosphonic group which can be converted into a lower alkyl ester; and $R^5$ represents a carboxyl group which can be converted into a lower alkyl ester, a lower alkanoylamino-lower alkyl ester, a phenyl lower alkyl ester, a lower alkoxyphenyl ester, a lower alkanoylaminophenyl ester or an indanyl ester; a carboxyl group which can be converted into an amide with ammonia; or a carboxyl group which can be converted into a hydroxamic acid, and salts thereof.

A compound wherein, in the compound (a), $R^1$ represents a carboxyl group which can be converted into a lower alkyl ester, a lower alkanoylamino-lower alkyl ester, a phenyl lower alkyl ester, a lower alkoxyphenyl ester, a lower alkanoylaminophenyl ester or an indanyl ester; a carboxyl group which can be converted into a hydroxamic acid; or a phosphonic group which can be converted into a lower alkyl ester; and $R^5$ represents a carboxyl group which can be converted into a lower alkyl ester, a phenyl lower alkyl ester or a lower alkanoylaminophenyl ester, and salts thereof.

A compound wherein, in the compound (a), $R^1$ represents a carboxyl group which can be converted into an ethyl ester, a butyl ester, an isopropyl ester, an isobutyl ester, a tert-butyl ester, an acetamidoethyl ester, a benzyl ester, a methoxyphenyl ester, an acetamidophenyl ester or an indanyl ester; a carboxyl group which can be converted into a hydroxamic acid; or a phosphonic group which can be converted into an ethyl ester; and $R^5$ represents a carboxyl group which can be converted into a methyl ester, a benzyl ester or an acetamidophenyl ester, and salts thereof.

A compound wherein, in the compound (a), $R^1$ represents a carboxyl group which can be converted into a lower alkyl ester, a phenyl lower alkyl ester, a lower alkoxyphenyl ester or an indanyl ester; and $R^5$ represents a carboxyl group which can be converted into a lower alkyl ester or a phenyl lower alkyl ester, and salts thereof.

A compound wherein, in the compound (a), $R^1$ represents a carboxyl group which can be converted into an ethyl ester, a butyl ester, an isopropyl ester, an isobutyl ester, a tert-butyl ester, a benzyl ester, a methoxyphenyl ester or an indanyl ester; and $R^5$ represents a carboxyl group which can be converted into a methyl ester or a benzyl ester, and salts thereof.

A compound wherein, in the compound (a), $R^3$ represents a lower alkyl group or a phenyl lower alkyl group; and $R^4$ represents a group represented by the above general formula [XI], [XII] or [XIII] (wherein $R^6$ represents a hydrogen atom or a nitro group; $R^7$ represents a hydrogen atom, a halogen atom, a lower alkyl group, a hydroxy group, a lower alkoxy group, a nitro group, an amino group or a phenyl group; $R^8$ and $R^9$ each represents a hydrogen atom; and $R^{10}$ represents a hydrogen atom, a halogen atom or a lower alkoxy group), and salts thereof.

A compound wherein, in the compound (a), $R^3$ represents a lower alkyl group; and $R^4$ represents a group represented by the above general formula [XI], [XII] or [XIII] (wherein $R^6$ represents a hydrogen atom or a nitro group; $R^7$ represents a hydrogen atom, a halogen atom, a lower alkyl group, a lower alkoxy group or a phenyl group; $R^8$ and $R^9$ each represents a hydrogen atom; and $R^{10}$ represents a hydrogen atom, a halogen atom or a lower alkoxy group), and salts thereof.

A compound wherein, in the compound (a), $R^3$ represents an isobutyl group; and $R^4$ represents a biphenylyl group, a fluorobiphenylyl group, a chlorobiphenylyl group, methylbiphenylyl group, a methoxybiphenylyl group, a nitrobiphenylyl group, a terphenylyl group, a naphthylphenyl group, a naphthyl group, a bromonaphthyl group or a methoxynaphthyl group, and salts thereof.

A compound wherein, in the compound (a), $R^3$ represents a lower alkyl group; and $R^4$ represents a group represented by the above general formula [XI] or [XIII] (wherein $R^6$ represents a hydrogen atom; $R^7$ represents a hydrogen atom, a halogen atom, a lower alkoxy group or a phenyl group; and $R^{10}$ represents a hydrogen atom or a lower alkoxy group), and salts thereof.

A compound wherein, in the compound (a), $R^3$ represents an isobutyl group; and $R^4$ represents a biphenylyl group, a fluorobiphenylyl group, a methoxybiphenylyl group, a terphenylyl group, a naphthyl group or a methoxynaphthyl group, and salts thereof.

A compound wherein, in the compound (a), $R^2$ represents a hydrogen atom, a lower alkyl group, a phenyl lower alkyl group, a lower alkoxy group or a phenyl lower alkoxy group; $R^3$ represents a lower alkyl group or a phenyl lower alkyl group; and $R^4$ represents a group represented by the above general formula [XI], [XII] or [XIII] (wherein $R^6$ represents a hydrogen atom or a nitro group; $R^7$ represents a hydrogen atom, a halogen atom, a lower alkyl group, a hydroxy group, a lower alkoxy group, a nitro group, an amino group or a phenyl group; $R^8$ and $R^9$ each represents a hydrogen atom; and $R^{10}$ represents a hydrogen atom, a halogen atom or a lower alkoxy group), and salts thereof.

A compound wherein, in the compound (a), $R^2$ represents a hydrogen atom, a lower alkyl group, a phenyl lower alkyl group or a phenyl lower alkoxy group; $R^3$ represents a lower alkyl group; and $R^4$ represents a group represented by the above general formula [XI], [XII] or [XIII] (wherein $R^6$ represents a hydrogen atom or a nitro group; $R^7$ represents a hydrogen atom, a halogen atom, a lower alkyl group, a lower alkoxy group or a phenyl group; $R^8$ and $R^9$ each represents a hydrogen atom; and $R^{10}$ represents a hydrogen atom, a halogen atom or a lower alkoxy group), and salts thereof.

A compound wherein, in the compound (a), $R^2$ represents a hydrogen atom, an isopentyl group, a benzyl group, a phenethyl group, a phenylpropyl group, a phenylbutyl group or a benzyloxy group; $R^3$ represents an isobutyl group; and $R^4$ represents a biphenylyl group, a fluorobiphenylyl group, a chlorobiphenylyl group, a methylbiphenylyl group, a methoxybiphenylyl group, a nitrobiphenylyl group, a terphenylyl group, a naphthylphenyl group, a naphthyl group, a bromonaphthyl group or a methoxynaphthyl group, and salts thereof.

A compound wherein, in the compound (a), $R^2$ represents a hydrogen atom, a lower alkyl group, a phenyl lower alkyl group or a phenyl lower alkoxy group; $R^3$ represents a lower alkyl group; and $R^4$ represents a group represented by the above general formula [XI] or [XIII] (wherein $R^6$ represents a hydrogen atom; $R^7$ represents a hydrogen atom, a halogen atom, a lower alkoxy group or a phenyl group; and $R^{10}$ represents a hydrogen atom or a lower alkoxy group), and salts thereof.

A compound wherein, in the compound (a), $R^2$ represents a hydrogen atom, an isopentyl group, a benzyl group, a phenethyl group, a phenylpropyl group, a phenylbutyl group or a benzyloxy group; $R^3$ represents an isobutyl group; and $R^4$ represents a biphenylyl group, a fluorobiphenylyl group, a methoxybiphenylyl group, a terphenylyl group, a naphthyl group or a methoxynaphthyl group, and salts thereof.

Preferred examples of the present compound include the followings.

Compound (b) of the above general formula [I] wherein $R^1$ represents a carboxyl group which can be converted into a lower alkyl ester, a lower alkanoylamino-lower alkyl ester, a phenyl lower alkyl ester, a lower alkoxyphenyl ester, lower alkanoylaminophenyl ester or an indanyl ester; a carboxyl group which can be converted into an amide with ammonia; a carboxyl group which can be converted into a hydroxamic acid; or a phosphonic group which can be converted into a lower alkyl ester; $R^2$ represents a hydrogen atom, a lower alkyl group, phenyl lower alkyl group, lower alkoxy group or a phenyl lower alkoxy group; $R^3$ represents a lower alkyl group or a phenyl lower alkyl group; $R^5$ represents a carboxyl group which can be converted into a lower alkyl ester, a lower alkanoylamino-lower alkyl ester, a phenyl lower alkyl ester, a lower alkoxyphenyl ester, a lower alkanoylaminophenyl ester or an indanyl ester; a carboxyl group which can be converted into an amide with ammonia; or a carboxyl group which can be converted into a hydroxamic acid; $R^4$ represents a group represented by the above general formula [XI], [XII] or [XIII] (wherein $R^6$ represents a hydrogen atom or a nitro group; $R^7$ represents a hydrogen atom, a halogen atom, a lower alkyl group, a hydroxy group, a lower alkoxy group, a nitro group, an amino group or a phenyl group; $R^8$ and $R^9$ each represents a hydrogen atom; and $R^{10}$ represents a hydrogen atom, a halogen atom or a lower alkoxy group); "A" represents a lower alkylene group; and "n" represents 1, and salts thereof.

Compound (c) of the above general formula [I] wherein $R^1$ represents a carboxyl group which can be converted into a lower alkyl ester, a lower alkanoylamino-lower alkyl ester, a phenyl lower alkyl ester, a lower alkoxyphenyl ester, a lower alkanoylaminophenyl ester or an indanyl ester; a carboxyl group which can be converted into a hydroxamic acid; or a phosphonic group which can be converted into a lower alkyl ester; $R^2$ represents a hydrogen atom, a lower alkyl group, phenyl lower alkyl group or a phenyl lower alkoxy group; $R^3$ represents a lower alkyl group; $R^5$ represents a carboxyl group which can be converted into a lower alkyl ester, a phenyl lower alkyl ester or a lower alkanoylaminophenyl ester; $R^4$ represents a group represented by the above general formula [XI], [XII] or [XIII] (wherein $R^6$ represents a hydrogen atom or a nitro group; $R^7$ represents a hydrogen atom, a halogen atom, a lower alkyl group, a lower alkoxy group or a phenyl group; $R^8$ and $R^9$ each represents a hydrogen atom; and $R^{10}$ represents a hydrogen atom, a halogen atom or a lower alkoxy group); "A" represents a lower alkylene group; and "n" represents 1, and salts thereof.

A compound wherein, in the compound (c), $R^1$ represents a carboxyl group which can be converted into an ethyl ester, a butyl ester, an isopropyl ester, an isobutyl ester, a tert-butyl ester, an acetamidoethyl ester, a benzyl ester, a methoxyphenyl ester, an acetamidophenyl ester or an indanyl ester; a carboxyl group which can be converted into a hydroxamic acid; or a phosphonic group which can be converted into an ethyl ester; $R^2$ represents a hydrogen atom, an isopentyl group, a benzyl group, a phenethyl group, a phenylpropyl group, a phenylbutyl group or a benzyloxy group; $R^3$ represents an isobutyl group; $R^4$ represents a biphenylyl group, a fluorobiphenylyl group, a chlorobiphenylyl group, a methylbiphenylyl group, a methoxybiphenylyl group, a nitrobiphenylyl group, a terphenylyl group, a naphthylphenyl group, a naphthyl group, a bromonaphthyl group or a methoxynaphthyl group; $R^5$ represents a carboxyl group which can be converted into a methyl ester, a benzyl ester or an acetamidophenyl ester; and "A" represents a methylene group, and salts thereof.

Compound (d) of the above general formula [I] wherein $R^1$ represents a carboxyl group which can be converted into an a lower alkyl ester, a phenyl lower alkyl ester, a lower alkoxyphenyl ester or an indanyl ester; $R^2$ represents a hydrogen atom, a lower alkyl group, a phenyl lower alkyl group or a phenyl lower alkoxy group; $R^3$ represents a lower alkyl group; $R^5$ represents a carboxyl group which can be converted into a lower alkyl ester or a phenyl lower alkyl ester; and $R^4$ represents a group represented by the above general formula [XI] or [XIII] (wherein $R^6$ represents a hydrogen atom; $R^7$ represents a hydrogen atom, a halogen atom, a lower alkoxy group or a phenyl group; $R^{10}$ represents a hydrogen atom or a lower alkoxy group; "A" represents a lower alkylene group; and "n" represents 1), and salts thereof.

A compound wherein, in the compound (d), $R^1$ represents a carboxyl group which can be converted into an ethyl ester, a butyl ester, an isopropyl ester, an isobutyl ester, a tert.-butyl ester, a benzyl ester, a methoxyphenyl ester or an indanyl ester; $R^2$ represents a hydrogen atom, an isopentyl group, a benzyl group, a phenethyl group, a phenylpropyl group, a phenylbutyl group or a benzyloxy group; $R^3$ represents an isobutyl group; $R^4$ represents a biphenylyl group, a fluorobiphenylyl group, a methoxybiphenylyl group, a terphenylyl group, a naphthyl group or a methoxynaphthyl group; $R^5$ represents a carboxyl group which can be converted into a methyl ester or a benzyl ester; and "A" represents a methylene group, and salts thereof.

Preferred examples of the present compound include 3-(4-biphenylyl)-2-[3-(2-carboxyethyl)-3-isobutylureido] propionic acid (formula [II] described hereinafter), 3-(4-biphenylyl)-2-[3-(2-carboxy-5-methylhexyl)-3-isobutylureido]propionic acid (formula [III] described hereinafter), 3-(4-biphenylyl)-2-[3-(2-carboxy-4-phenylbutyl)-3-isobutylureido]propionic acid (formula [IV] described hereinafter), 2-[3-(2-benzyloxy-2-carboxyethyl)-3-isobutylureido]-3-(4-biphenylyl)propionic acid (formula [V] described hereinafter), 2-[3-(2-carboxyethyl)-3-isobutylureido]-3-(2-naphthyl)propionic acid (formula [VI] described hereinafter), 2 -[3-(2-carboxy-4-phenylbutyl)-3-isobutylureido]-3-(2-naphthyl)propionic acid (formula [VII] described hereinafter), salts thereof, single diastereo isomers thereof, optical isomers thereof and, furthermore, (2S)-3-(4-biphenylyl)-2-[3-(2-butoxycarbonylethyl)-3-isobutylureido] propionic acid (formula [XIV] described hereinafter) and salts thereof.

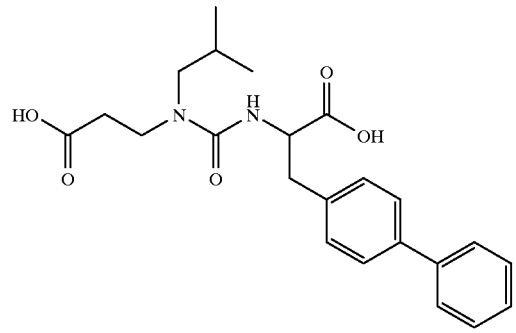

[II]

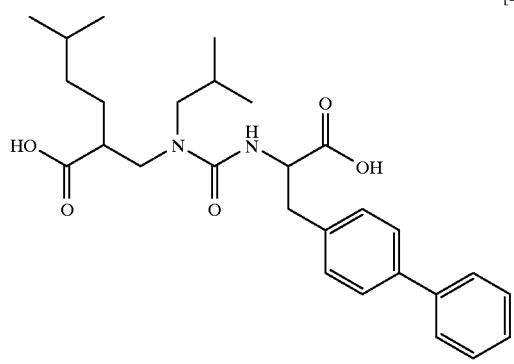
[III]

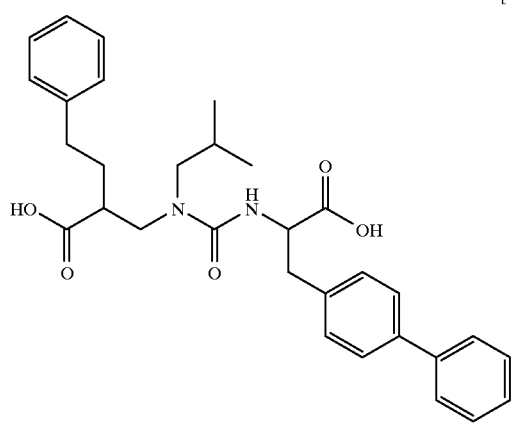
[IV]

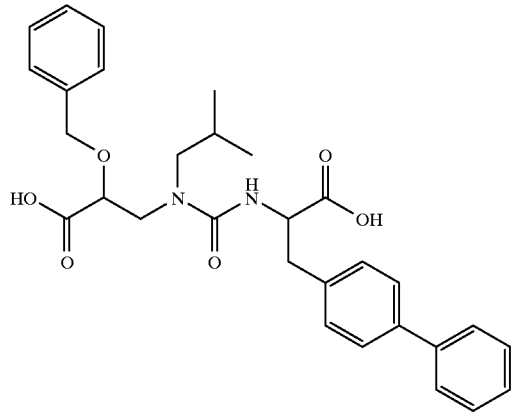
[V]

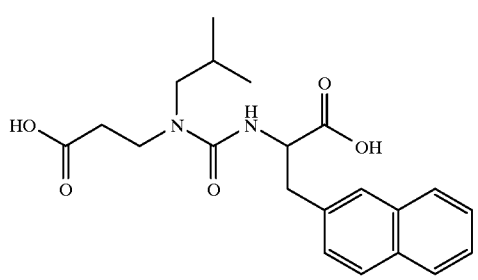
[VI]

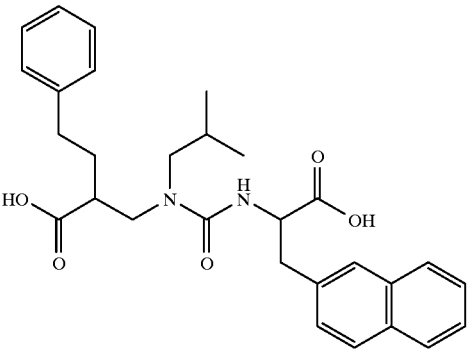
[VII]

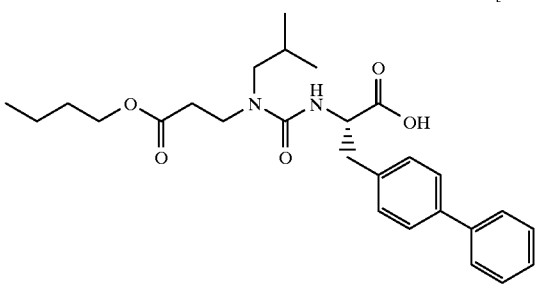
[XIV]

The typical synthesis method of the present compound will be shown hereinafter.

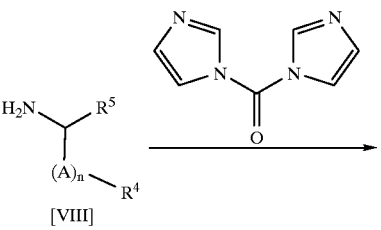
[VIII]

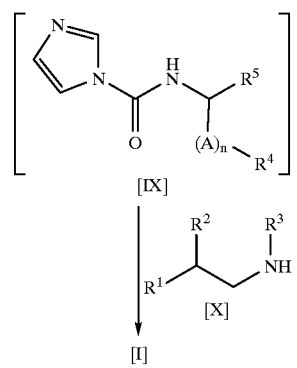
[IX]

[X]

[I]

This method comprises reacting a compound represented by the general formula [VIII] with 1,1'-carbonyldiimidazole in the presence of a base such as imidazole to lead to a compound of the general formula [IX], reacting the resultant compound with a compound of the general formula [X] to form an urea, thereby obtaining the present compound (general formula [I]). Incidentally, some of the compound represented by the general formula [VIII] can be synthesized from tyrosine by a method reported by Shieh et al. (J. Org. Chem., 57, 379–381 (1992)), or synthesized through an azide body using a method reported by Evans et al. (J. Am. Chem. Soc., 109, 6881–6883 (1987)).

If necessary, the carboxyl group can be converted into an ester or an amide by using a conventional method. To the contrary, the ester or amide can be hydrolyzed by using a conventional method, to form a carboxylic acid.

If necessary, the carboxyl group can be converted into an ester or an amide and the phosphonic group can be converted into an ester by using a conventional method. To the contrary, the ester or amide can be hydrolyzed by using a conventional method, to form a carboxylic acid or a phosphonic acid.

The compound obtained by the above method can be converted into the salts described above by a conventional method.

Diastereo isomers and optical isomers are present in the compound represented by the general formula [I], and they are included in the present invention. When using an optically active raw material, a single diastereo isomer and a single optical isomer are obtained. On the other hand, when using a racemic body as the raw material, each isomer can be separated by using a conventional method, for example, a method of using a reagent for optical resolution. The present compound may take the form of a hydrate.

In order to examine the utility of the present compound, studies were made on an action of the present compound to endopeptidase 24.11. The details will be shown in the pharmacological test described hereinafter. N-Dansyl-D-alanyl-glycyl-p-nitrophenylalanyl-glycine known as a substrate of endopeptidase 24.11 was used in the study. As a result, the present compound exhibited strong inhibition activity to endopeptidase 24.11.

Endopeptidase 24.11, which is one of neutral endopeptidases, is an enzyme which exists in the living body and is concerned in various biofunctions. It has already been reported that the compounds inhibiting endopeptidase 24.11 increase total urine volume, urinary sodium excretion, urinary ANP excretion and urinary cyclic GMP excretion in heart failure models (J. Cardiovasc. Pharmacol., 19, 635–640 (1992), J. Pharmacol. Exp. Ther., 266, 872–883 (1993)), that they exhibit a hypotensive effect in hypertensive models (J. Pharmacol. Exp. Ther., 265, 1339–1347 (1993)), that they increase urinary sodium excretion in models with renal ablation (Circ. Res., 65, 640–646 (1989), that they exhibit an effect of improvement of acute diarrhea (Gut, 33, 753–758 (1992)), and that they exhibit an analgestic effect (Nature, 288, 286–288 (1980). It has also been reported that bonbesin which reduces food intake (J. Clin. Endocrinol. Metab., 76, 1495–1498 (1993)) is hydrolysed by endopeptidase 24.11 (Proc. Natl. Acad. Sci., 88, 10662–10666 (1991)), and that an endopeptidase 24.11 activity in blood and synovial fluid of patients with rheumatoid arthritis is distinctly high (Rheumatol. Int., 13, 1–4 (1993)). Therefore, the compounds inhibiting endopeptidase 24.11 are expected to have wide medical uses as therapeutic agents for cardiovascular diseases such as heart failure and hypertension, renal diseases such as renal failure, gastroenteric disorders such as diarrhea and hyperchlorhydria, endocrine and metabolic diseases such as obesity, and autoimmune diseases such as rheumatic disease, and as analgestics for pains such as myosalgia and migraine.

As mentioned above, the present compound exhibits an excellent inhibitory effect on endopeptidase 24.11 and is useful for various diseases in which endopeptidase 24.11 is concerned.

In addition, studying an effect of the present compound on the angiotensin-converting enzyme, an excellent inhibitory activity was observed. This result suggests that the present compound is particularly useful as therapeutic agents for cardiovascular disease such as heart failure and hypertension.

The present compound can be administered orally or parenterally. Examples of dosage forms are tablets, capsules, granules, powders, injections, etc. The present compound can be formulated into preparations by conventional methods. For example, oral preparations such as a tablet, a capsule, granules and powders can be produced by adding optionally diluents such as lactose, crystalline cellulose or starch; lubricants such as magnesium stearate or talc; binders such as hydroxypropylcellulose or polyvinyl pyrrolidone; a disintegrator such as calcium carboxymethylcellulose or low-substituted hydroxypropylmethylcellulose; coating agent such as hydroxypropylmethylcellulose, macrogol or silicone resin.

The dose of the present compound can be selected suitably according to the symptom, age, dosage form and the like. In case of the oral preparation, the present compound may be administered 1 to several times per day with a daily dose of 0.1 to 6000 mg, preferably 1 to 600 mg.

BEST MODE FOR CARRYING OUT THE INVENTION

Examples of preparations and formulations of the compounds of the invention are shown below. These examples do not limit the scope of the invention, but are intended to make the invention more clearly understandable.

Preparation of Compounds

Reference Example 1

Benzyl(2S)-2-amino-3-(4-biphenylyl)propionate hydrochloride (reference compound No. 1-1)

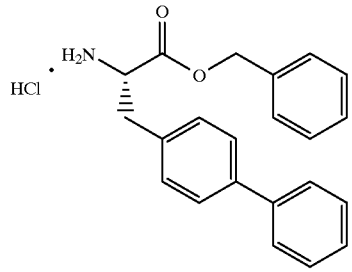

1) To a solution of N-tert.-butoxycarbonyl-L-tyrosine benzyl ester (1.0 g) in methylene chloride (4.2 ml) is added pyridine (1.1 ml), and the mixture is stirred. To the reaction mixture is added trifluoromethanesulfonic anhydride (0.52 ml) under ice-cooling. The mixture is further stirred for one hour under ice-cooling. To the reaction mixture is added water, and the whole is extracted with methylene chloride. The organic layer is sequentially washed with 0.1 N sodium hydroxide and a 10% aqueous citric acid solution, dried over anhydrous magnesium sulfate, and concentrated in vacuo. The oily residue is purified by silica gel column chromatography to give 994 mg (73.1%) of N-tert.-butoxycarbonyl-(4-trifluoromethanesulfonyloxy)-L-phenylalanine benzyl ester.

mp 60.0–60.9° C.

$[\alpha]_D^{20}$ −10.8° (c=1.0, methanol)

IR (KBr, cm$^{-1}$) 3402, 2984, 1743, 1690, 1521, 1424, 1250, 1201, 1143, 1012, 902, 639.

2) To a solution of N-tert.-butoxycarbonyl-(4-trifluoromethanesulfonyloxy)-L-phenylalanine benzyl ester (900 mg), phenylboric acid (435 mg) and potassium carbonate (370 mg) in toluene (18 ml) is added tetrakis(triphenylphosphine)palladium(0) (50 mg) under a nitrogen atmosphere. The mixture is stirred at 85° C. for two hours. After cooling, to the reaction mixture is added water, and the whole is extracted with ethyl acetate. The organic layer is sequentially washed with a saturated sodium bicarbonate solution, a 10% aqueous citric acid solution and a saturated sodium chloride solution, dried over anhydrous magnesium sulfate and concentrated in vacuo. The oily residue is purified by silica gel column chromatography to give 553 mg (71.6%) of benzyl(2S)-3-(4-biphenylyl)-2-tert.-butoxycarbonylaminopropionate.

mp 98.3–100.1° C.

$[\alpha]_D^{20}$ −8.2° (c=0.52, methanol)

IR (KBr, cm$^{-1}$) 3369, 2983, 1747, 1684, 1514, 1488, 1250, 1168, 1008, 763, 695.

3) To a solution of benzyl(2S)-3-(4-biphenylyl)-2-tert.-butoxycarbonylaminopropionate (500 mg) in ethyl acetate (2.3 ml) is added 4.1 N hydrochloric acid/ethyl acetate (2.8 ml). The mixture is stirred at room temperature for two hours and 40 minutes. The reaction mixture is concentrated in vacuo to give 378 mg (88.6%) of the titled compound (reference compound No. 1-1). mp 235.0–236.2° C. (decomp.)

$[\alpha]_D^{20}$ −22.0° (c=1.0, methanol)

IR (KBr, cm$^{-1}$) 3152, 2798, 2673, 1746, 1606, 1492, 1372, 1233, 1194, 761, 696.

The following compounds can be prepared by a method similar to Reference Example 1.

Benzyl(2S)-2-amino-3-[4-(4'-fluoro)biphenylyl]propionate hydrochloride (reference compound No. 1-2)
mp 244.0–245.5° C. (decomp.)
$[\alpha]_D^{20}$ −19.2° (c=1.0, methanol)
IR (KBr, cm$^{-1}$) 3155, 3000, 2800, 2009, 1746, 1607, 1493, 1233, 1194, 1158, 823, 803, 747, 699, 567, 548.

Benzyl(2S)-2-amino-3-[4-(4'-chloro)biphenylyl]propionate hydrochloride (reference compound No. 1-3)
mp 225.0–228.5° C. (decomp.)
$[\alpha]_D^{20}$ −15.8° (c=0.36, methanol)
IR (KBr, cm$^{-1}$) 2850, 1746, 1486, 1372, 1234, 1142, 1095, 940.

Benzyl(2S)-2-amino-3-[4-(4'-methyl)biphenylyl]propionate hydrochloride (reference compound No. 1-4)
mp 240° C. (decomp.)
$[\alpha]_D^{20}$ −22.1° (c=0.98, methanol)
IR (KBr, cm$^{-1}$) 3145, 2797, 1747, 1493, 1372, 1234, 1194, 802, 607.

Benzyl(2S)-2-amino-3-[4-(3'-methoxy)biphenylyl]propionate hydrochloride (reference compound No. 1-5)
mp 213.0–214.5° C. (decomp.)
$[\alpha]_D^{20}$ −17.9° (c=1.0, methanol)
IR (KBr, cm$^{-1}$) 3149, 2834, 1749, 1608, 1496, 1406, 1219, 1141, 1058.

Benzyl(2S)-2-amino-3-[4-(2'-methoxy)biphenylyl]propionate hydrochloride (reference compound No. 1-6)
mp 183.0–189.5° C. (decomp.)
$[\alpha]_D^{20}$ −18.3° (c=0.48, methanol)
IR (KBr, cm$^{-1}$) 3155, 2849, 2646, 1737, 1496, 1435, 1262, 1231, 1205.

Benzyl(2S)-2-amino-3-[4-(2-nitro)biphenylyl]propionate hydrochloride (reference compound No. 1-7)
mp 100° C. (decomp.)
$[\alpha]_D^{20}$ −15.5° (c=0.98, methanol)

IR (KBr, cm$^{-1}$) 3406, 3299, 2865, 1749, 1530, 1347, 1235, 757, 694.

Benzyl(2RS)-2-amino-3-(3-biphenylyl)propionate hydrochloride (reference compound No. 1-8)
mp 117.0–121.5° C.
IR (KBr, cm$^{-1}$) 2863, 1964, 1744, 1575, 1506, 1227.

Benzyl(2S)-2-amino-3-(1,1':4',1''-terphenyl-4-yl)propionate hydrochloride (reference compound No. 1-9)
mp 280° C. (decomp.)
$[\alpha]_D^{20}$ −6.5° (c=0.32, dimethyl sulfoxide)
IR (KBr, cm$^{-1}$) 3148, 3003, 2801, 2676, 1746, 1493, 1372, 1233, 761, 697.

Benzyl(2S)-2-amino-3-(1,1':2',1''-terphenyl-4-yl)propionate hydrochloride (reference compound No. 1-10)
mp 167.0–168.2° C.
$[\alpha]_D^{20}$ +2.6° (c=1.1, methanol)
IR (KBr, cm$^{-1}$) 3397, 2912, 2000, 1744, 1641, 1590, 1499, 1259, 748, 739.

Benzyl(2S)-2-amino-3-[4-(2-naphthyl)phenyl]propionate hydrochloride (reference compound No. 1-11)
mp 222.0–223.0° C. (decomp.)
$[\alpha]_D^{20}$ −23.6° (c=1.0, methanol)
IR (KBr, cm$^{-1}$) 3148, 2852, 1747, 1492, 1371, 1233, 940, 840, 802, 745, 697.

Benzyl(2S)-2-amino-3-[4-(1-naphthyl)phenyl]propionate hydrochloride (reference compound No. 1-12)
mp 169.2–170.5° C.
$[\alpha]_D^{20}$ −15.3° (c=1.0, methanol)
IR (KBr, cm$^{-1}$) 3149, 2856, 2012, 1747, 1514, 1490, 1375, 1239, 1199, 792, 698.

Benzyl(2S)-2-amino-3-[4-(4'-methyl-2-nitro)biphenylyl]propionate hydrochloride (reference compound No. 1-13)

Benzyl(2S)-2-amino-3-[4-(4'-hydroxy)biphenylyl]propionate hydrochloride (reference compound No. 1-14)

Benzyl(2S)-2-amino-3-[4-(4'-methoxy)biphenylyl]propionate hydrochloride (reference compound No. 1-15)

Benzyl(2S)-2-amino-3-[4-(4'-nitro)biphenylyl]propionate hydrochloride (reference compound No. 1-16)

Benzyl(2S)-2-amino-3-[4-(3'-nitro)biphenylyl]propionate hydrochloride (reference compound No. 1-17)

Reference Example 2

(2S)-2-Azido-3-[2-(1-bromo)naphthyl]propionic acid (reference compound No. 2-1)

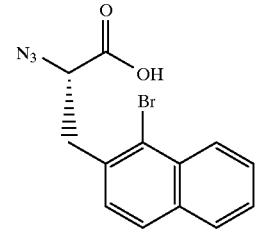

1) To a solution of N-ethyldiisopropylamine (560 μl) and pivaloyl chloride (340 μl) in tetrahydrofuran (3 ml) is added a solution of 3-[2-(1-bromo)naphthyl]propionic acid (1.0 g) in tetrahydrofuran (4 ml) dropwise while stirring under a nitrogen atmosphere and dryice-cooling. The mixture is further stirred under ice-cooling for one hour. To a solution of 4-benzyloxazolidine-2-one (478 mg) in tetrahydrofuran (10 ml) is added 1.6 M n-butyl lithium/hexane (1.69 ml) dropwise while stirring under a nitrogen atmosphere and dryice-cooling. The mixture is further stirred under dryice-cooling for 25 minutes. To the latter reaction mixture is added the former reaction mixture dropwise while stirring under a nitrogen atmosphere and dryice-cooling. The mixture is further stirred under ice-cooling for 75 minutes. To the reaction mixture is added water, and the obtained mixture is concentrated in vacuo. To the oily residue is added water, and the whole is extracted with diethyl ether. The organic layer is washed with a saturated sodium chloride solution, dried over anhydrous sodium sulfate and concentrated in vacuo to give 907 mg (77%) of (4S)-4-benzyl-3-[3-[2-(1-bromo)naphthyl]propionyl]oxazolidine-2-one.

mp 101.7–103.5° C.

$[\alpha]_D^{20}$ +80.4° (c=0.17, methanol)

IR (KBr, cm$^{-1}$) 2995, 1781, 1699, 1390, 1205, 823, 804, 766, 741.

2) To a solution of (4S)-4-benzyl-3-[3-[2-(1-bromo) naphthyl]propionyl]oxazolidine-2-one (877 mg) in tetrahydrofuran (30 ml) are added 0.5 M potassium hexamethyldisilylazide/toluene (4.2 ml) and a solution of 2, 4, 6-triisopropylbenzenesulfonylazide (774 mg) in tetrahydrofuran (3 ml) under a nitrogen atmosphere and dryice-cooling. The mixture is stirred for two minutes. To the reaction mixture is added acetic acid (527 μl) and the mixture is stirred at 35–40° C. for 30 minutes. The reaction mixture is extracted with methylene chloride. The organic layer is sequentially washed with a saturated sodium bicarbonate solution and a saturated sodium chloride solution, dried over anhydrous sodium sulfate and concentrated in vacuo. The oily residue is purified by silica gel column chromatography to give 902 mg (94%) of (4S)-3-[2-azido-3-[2-(1-bromo)naphthyl]propionyl]-4-benzyloxazolidine-2-one as amorphous powder.

$[\alpha]_D^{20}$ +80.6° (c=1.0, methanol)

IR (KBr, cm$^{-1}$) 3304, 3028, 2963, 2108, 1781, 1704, 1390, 1212, 1111, 811, 754, 702.

3) To a solution of (4S)-3-[2-azido-3-[2-(1-bromo) naphthyl]propionyl]-4-benzyloxazolidine-2-one (825 mg) in tetrahydrofuran (5 ml)-water (1.2 ml) is added lithium hydroxide monohydrate (124 mg) in 30% hydrogen peroxide (836 μl) under ice-cooling. The mixture is stirred for three hours. To the reaction mixture is added 1 M sodium sulfate. The mixture is stirred and concentrated in vacuo. The oily residue is acidified with 6 N hydrochloric acid, and the whole is extracted with chloroform. The organic layer is dried over anhydrous sodium sulfate and concentrated in vacuo. The oily residue is purified by silica gel column chromatography to give 411 mg (87%) of the titled compound (reference compound No. 2-1).

mp 84.2–91.5° C.

$[\alpha]_D^{20}$ –85.6° (c=1.0, methanol)

IR (KBr, cm$^{-1}$) 2900, 2132, 1722, 1424, 1287, 1221, 899, 806, 747.

The following compound can be prepared by a method similar to Reference Example 2.

(2S)-2-Azido-3-[2-(6-methoxy)naphthyl]propionic acid (reference compound No. 2-2)
mp 111.8–115.6° C.
$[\alpha]_D^{20}$ –48.8° (c=0.53, methanol)
IR (KBr, cm$^{-1}$) 2969, 2126, 1720, 1605, 1266, 1224, 1193, 1158, 1025, 857, 818.

Reference Example 3

Methyl(2S)-2-amino-3-[2-(1-bromo)naphthyl]propionate hydrochloride (reference compound No. 3-1)

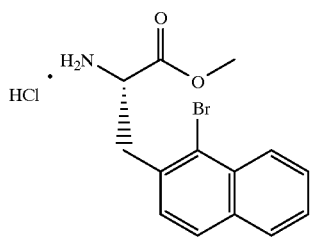

1) To a solution of (2S)-2-azido-3-[2-(1-bromo)naphthyl] propionic acid (reference compound No. 2-1, 460 mg) in methanol (30 ml) is added p-toluenesulfonic acid monohydrate (273 mg). The mixture is refluxed for one hour. After cooling, the reaction mixture is concentrated in vacuo. The oily residue is purified by silica gel column chromatography to give methyl(2S)-2-azido-3-[2-(1-bromo)naphthyl] propionate.

$[\alpha]_D^{20}$ –45.1° (c=1.0, methanol)

IR (film, cm$^{-1}$) 3294, 3056, 2957, 2113, 1745, 1599, 1557, 1502, 1440, 1261, 1209, 814, 748.

2) Water (39 μl) is added to a solution of methyl(2S)-2-azido-3-[2-(1-bromo)naphthyl]propionate (364 mg) and triphenylphosphine (428 mg) in tetrahydrofuran (10 ml). The mixture is stirred at room temperature for 2.5 hours. The reaction mixture is concentrated in vacuo, and the oily residue is dissolved in tetrahydrofuran (10 ml). To the solution are added triethylamine (250 μl) and di-tert.-butyl dicarbonate (250 μl) under ice-cooling. The mixture is stirred at room temperature for two hours and refluxed for three hours. The reaction mixture is concentrated in vacuo. To the oily residue is added a 10% aqueous citric acid solution, and the whole is extracted with ethyl acetate. The organic layer is sequentially washed with water and a saturated sodium chloride solution, dried over anhydrous sodium sulfate and concentrated in vacuo. The oily residue is purified by silica gel column chromatography to give methyl(2S)-3-[2-(1-bromo)naphthyl]-2-tert.-butoxycarbonylaminopropionate. The compound is dissolved in 4.1 N hydrochloric acid/ethyl acetate (3 ml). The solution is stirred at room temperature overnight. The reaction mixture is concentrated in vacuo to give 71 mg (19%) of the titled compound (reference compound No. 3-1).

mp 208–213° C. (decomp.)

$[\alpha]_D^{20}$ –35.6° (c=0.047, dimethyl sulfoxide)

IR (KBr, cm$^{-1}$) 3381, 2949, 2828, 2631, 2031, 1750, 1502, 1445, 1234, 742.

Reference Example 4

Benzyl(2S)-2-amino-3-[2-(6-methoxy)naphthyl] propionate p-toluenesulfonate (reference compound No. 4-1)

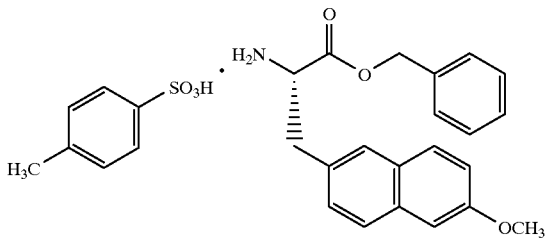

To a solution of (2S)-2-azido-3-[2-(6-methoxy)naphthyl] propionic acid (reference compound No. 2-2, 495 mg) in tetrahydrofuran (20 ml)-1 N hydrochloric acid (3 ml) is added 5% palladium on activated carbon (50 mg) under a nitrogen atmosphere. The mixture is stirred under a hydrogen atmosphere for one hour and 40 minutes. The palladium on activated carbon is removed by Celite filtration and the filtrate is concentrated in vacuo. The oily residue is dissolved in benzene (18 ml). To the solution are added p-toluenesulfonic acid monohydrate (273 mg) and benzyl alcohol (3.8 ml). The mixture is refluxed for four hours. After cooling, the reaction mixture is concentrated in vacuo to give 6211 mg (67%) of the titled compound (reference compound No. 4-1).

mp 193.0–198.4° C.

$[\alpha]_D^{20}$ −26.2° (c=0.51, methanol)

IR (KBr, cm$^{-1}$) 3361, 3033, 2958, 1732, 1651, 1505, 1265, 1175, 752, 698.

EXAMPLE 1

Benzyl(2S)-3-(4-biphenylyl)-2-[3-(2-ethoxycarbonylethyl)-3-isobutylureido]propionate (compound No. 1-1)

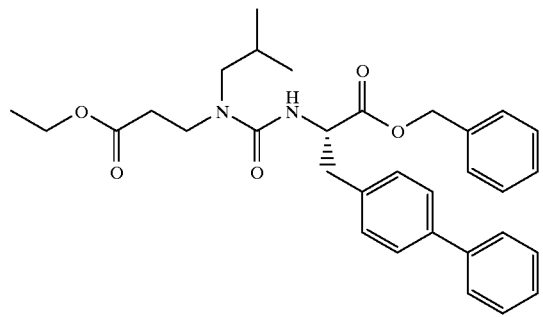

Tetrahydrofuran (14 ml) is added to a mixture of benzyl (2S)-2-amino-3-(4-biphenylyl)propionate hydrochloride (reference compound No. 1-1, 1 g), 1,1'-carbonyldiimidazole (529 mg) and imidazole (185 mg) under a nitrogen atmosphere. The mixture is stirred at room temperature for 20 minutes. To the reaction mixture is added ethyl 3-(N-isobutyl)aminopropionate hydrochloride (599 mg). The mixture is refluxed for one hour. After cooling, to the reaction mixture is added a 10% aqueous citric acid solution, and the whole is extracted with diethyl ether. The organic layer is sequentially washed with water and a saturated sodium chloride solution, dried over anhydrous magnesium sulfate and concentrated in vacuo. The oily residue is purified by silica gel column chromatography to give 1.42 g (98%) of the titled compound (compound No. 1-1).

$[\alpha]_D^{20}$ −26.8° (c=1.0, methanol)

IR (film, cm$^{-1}$) 3350, 3030, 2959, 2871, 1732, 1651, 1519, 1455, 1188.

The following compounds can be prepared by a method similar to Example 1.

Benzyl(2S)-3-(4-biphenylyl)-2-[3-(2-tert.-butoxycarbonylethyl)- 3-isobutylureido]propionate (compound No. 1-2)

$[\alpha]_D^{20}$ −23.9° (c=0.98, methanol)

IR (film, cm$^{-1}$) 3350, 3029, 2961, 1726,1644, 1519, 1487, 1455.

Benzyl(2S)-2-[3-(2-benzyloxycarbonylethyl)-3-isobutylureido]-3-(4-biphenylyl)propionate (compound No.1-3)

$[\alpha]_D^{20}$ −29.9° (c=0.29, methanol)

IR (film, cm$^{-1}$) 3447, 3030, 2958, 1733, 1651, 1516, 1487, 1386, 1259, 1173, 756, 698.

Benzyl(2S)-3-(4-biphenylyl)-2-[3-[(2RS)-2-tert.-butoxycarbonyl-5-methylhexyl]-3-isobutylureido] propionate (compound No. 1-4)

$[\alpha]_D^{20}$ −19.4° (c=1.1, methanol)

IR (film, cm$^{-1}$) 3448, 3359, 2957, 2869, 1723, 1651, 1511, 1152, 1008, 846, 757, 698.

Benzyl(2S)-3-(4-biphenylyl)-2-[3-[(2RS)-2-tert.-butoxycarbonyl-3-phenylpropyl]-3-isobutylureido] propionate (compound No. 1-5)

$[\alpha]_D^{20}$ −11.6° (c=0.52, chloroform)

IR (film, cm$^{-1}$) 3448, 3360, 2961, 1724, 1650, 1514, 1455, 1368, 1253, 1152.

Benzyl(2S)-3-(4-biphenylyl)-2-[3-[(2RS)-2-ethoxycarbonyl-4-phenylbutyl]-3-isobutylureido] propionate (compound No. 1-6)

$[\alpha]_D^{20}$ −23.2° (c=0.53, methanol)

IR (film, cm$^{-1}$) 3447, 2957, 1729, 1650, 1513, 1454, 1256, 1185, 757, 698.

Benzyl(2S)-3-(4-biphenylyl)-2-[3-[(2RS)-2-tert.-butoxycarbonyl- 4-phenylbutyl]-3-isobutylureido] propionate (compound No. 1-7)

$[\alpha]_D^{20}$ −21.2° (c=1.0, methanol)

IR (film, cm$^{-1}$) 3448, 3358, 2959, 1723, 1650, 1511, 1454, 1256, 1150, 757, 698.

Benzyl(2S)-2-[3-[(2RS)-2-benzyloxycarbonyl-4-phenylbutyl]-3-isobutylureido]-3-(4-biphenylyl) propionate (compound No. 1-8)

$[\alpha]_D^{20}$ −20.3° (c=0.049, methanol)

IR (film, cm$^{-1}$) 3445, 3029, 2956, 1733, 1653, 1509, 1454, 1385, 1174, 754, 698.

Benzyl(2S)-3-(4-biphenylyl)-2-[3-[(2RS)-2-tert.-butoxycarbonyl-5-phenylpentyl]-3-isobutylureido] propionate (compound No. 1-9)

$[\alpha]_D^{20}$ −29.5° (c=0.073, methanol)

IR (film, cm$^{-1}$) 3366, 3028, 2958, 1722, 1651, 1505, 1367, 1152, 758, 698.

Benzyl(2S)-3-(4-biphenylyl)-2-[3-[(2RS)-2-tert.-butoxycarbonyl-6-phenylhexyl]-3-isobutylureido] propionate (compound No. 1-10)

$[\alpha]_D^{20}$ −20.1° (c=0.63, methanol)

IR (film, cm$^{-1}$) 3363, 2933, 1723, 1652, 1510, 1367, 1153, 756, 698.

Benzyl(2S)-2-[3-[(2RS)-2-benzyloxy-2-benzyloxycarbonylethyl]-3-isobutylureido]-3-(4-biphenylyl)propionate (compound No. 1-11)

$[\alpha]_D^{20}$ −15.2° (c=1.0, chloroform)

IR (film, cm$^{-1}$) 3342, 2957, 1742, 1657, 1514, 1455, 1251, 1172, 1114, 754, 698.

Benzyl(2S)-2-[3-(2-benzyloxycarbonylethyl)-3-isobutylureido]-3-[4-(4'-fluoro)biphenylyl]propionate (compound No. 1-12)

$[\alpha]_D^{20}$ -27.9° (c=0.48, methanol)
IR (film, cm$^{-1}$) 3359, 3032, 2958, 1736, 1650, 1498, 1455, 1386, 1173, 1008, 819, 752, 698.

Benzyl(2S)-2-[3-(2-benzyloxycarbonylethyl)-3-isobutylureido]-3-[4-(4'-chloro)biphenylyl]propionate (compound No. 1-13)
$[\alpha]_D^{20}$ -17.8° (c=0.29, chloroform)
IR (film, cm$^{-1}$) 3789, 3659, 2960, 1732, 1651, 1504, 1486, 1215, 1142, 1006.

Benzyl(2S)-2-[3-(2-benzyloxycarbonylethyl)-3-isobutylureido]-3-[4-(4'-methyl)biphenylyl]propionate (compound No. 1-14)
$[\alpha]_D^{20}$ -28.3° (c=1.4, methanol)
IR (film, cm$^{-1}$) 3447, 3030, 2958, 1731, 1645, 1501, 1182, 910, 809, 734, 699.

Benzyl(2S)-2-[3-(2-benzyloxycarbonylethyl)-3-isobutylureido]-3-[4-(3'-methoxy)biphenylyl]propionate (compound No. 1-15)

Benzyl(2S)-2-[3-(2-benzyloxycarbonylethyl)-3-isobutylureido]-3-[4-(2'-methoxy)biphenylyl]propionate (compound No. 1-16)
$[\alpha]_D^{20}$ -15.4° (c=0.74, chloroform)
IR (film, cm$^{-1}$) 3360, 3065, 2959, 1731, 1649, 1516, 1455, 1179.

Benzyl(2S)-2-[3-(2-benzyloxycarbonylethyl)-3-isobutylureido]-3-[4-(2-nitro)biphenylyl]propionate (compound No. 1-17)
$[\alpha]_D^{20}$ -38.6° (c=0.093, methanol)
IR (film, cm$^{-1}$) 2959, 1732, 1644, 1531, 1359, 1175, 756, 699.

Benzyl(2RS)-2-[3-(2-benzyloxycarbonylethyl)-3-isobutylureido]-3-(3-biphenylyl)propionate (compound No. 1-18)
IR (film, cm$^{-1}$) 3364, 2957, 1734, 1648, 1512, 1173, 755, 698.

Benzyl(2S)-2-[3-(2-benzyloxycarbonylethyl)-3-isobutylureido]-3-(1,1':4',1''-terphenyl-4-yl)propionate (compound No. 1-19)
mp 96.0–99.0° C.
$[\alpha]_D^{20}$ -20.1° (c=0.51, chloroform)
IR (KBr, cm$^{-1}$) 3385, 2954, 1734, 1626, 1519, 1366, 1291.

Benzyl(2S)-2-[3-(2-benzyloxycarbonylethyl)-3-isobutylureido]-3-(1,1':2',1''-terphenyl-4-yl)propionate (compound No. 1-20)
$[\alpha]_D^{20}$ -17.8° (c=0.67, methanol)
IR (film, cm$^{-1}$) 3368, 3032, 2958, 2362, 1733, 1651, 1514, 1475, 1386, 746, 699.

Benzyl(2S)-2-[3-(2-benzyloxycarbonylethyl)-3-isobutylureido]-3-[4-(2-naphthyl)phenyl]propionate (compound No. 1-21)
$[\alpha]_D^{20}$ -22.5° (c=0.48, chloroform)
IR (film, cm$^{-1}$) 3350, 3032, 2958, 1735, 1651, 1502, 1173, 751, 698.

Benzyl(2S)-2-[3-(2-benzyloxycarbonylethyl)-3-isobutylureido]-3-[4-(1-naphthyl)phenyl]propionate (compound No. 1-22)
$[\alpha]_D^{20}$ -28.3° (c=0.17, methanol)
IR (film, cm$^{-1}$) 3446, 2957, 1732, 1644, 1514, 1455, 1386, 1173, 779, 697.

Benzyl(2S)-2-[3-(2-ethoxycarbonylethyl)-3-isobutylureido]-3-(2-naphthyl)propionate (compound No. 1-23)
$[\alpha]_D^{20}$ -28.7° (C=0.98, chloroform)
IR (film, cm$^{-1}$) 3349, 2959, 1732, 1651, 1510, 1455, 1377, 1342, 1186, 747, 698.

Benzyl(2S)-2-[3-(2-benzyloxycarbonylethyl)-3-isobutylureido]-3-(2-naphthyl)propionate (compound No. 1-24)
$[\alpha]_D^{20}$ -24.1° (c=1.1, methanol)
IR (film, cm$^{-1}$) 3355, 2957, 1735, 1649, 1509, 1172.

Benzyl(2S)-3-(4-biphenylyl)-2-[3-[(2RS)-2-ethoxycarbonyl-4-phenylbutyl]-3-isobutylureido]propionate (compound No. 1-25)

Benzyl(2S)-2-[3-[(2RS)-2-tert.-butoxycarbonyl-4-phenylbutyl]-3-isobutylureido]-3-(2-naphthyl)propionate (compound No. 1-26)
$[\alpha]_D^{20}$ -20.5° (c=0.50, chloroform)
IR (film, cm$^{-1}$) 3445, 3361, 2958, 1718, 1653, 1507, 1454, 1367, 1150, 747, 698.

Benzyl(2S)-2-[3-[(2RS)-2-benzyloxy-2-benzyloxycarbonylethyl]-3-isobutylureido]-3-(2-naphthyl)propionate (compound No. 1-27)
$[\alpha]_D^{20}$ -21.8° (c=0.98, chloroform)
IR (film, cm$^{-1}$) 3343, 3062, 2958, 1742, 1651, 1511, 1455, 1175, 1115.

Methyl(2S)-2-[3-(2-benzyloxycarbonylethyl)-3-isobutylureido]-3-[2-(1-bromo)naphthyl]propionate (compound No. 1-28)
IR (film, cm$^{-1}$) 3366, 2955, 1732, 1644, 1519, 1176, 1074, 1029, 1002, 816, 750, 698.

Benzyl(2S)-2-[3-(2-benzyloxycarbonylethyl)-3-isobutylureido]-3-[2-(6-methoxy)naphthyl]propionate (compound No. 1-29)
$[\alpha]_D^{20}$ -26.2° (c=0.51, methanol)
IR (film, cm$^{-1}$) 3361, 3033, 2958, 1732, 1651, 1607, 1505, 1265, 1175, 853, 753, 698.

Benzyl(2S)-2-[3-(2-benzyloxycarbonylethyl)-3-isobutylureido]-3-(1-naphthyl)propionate (compound No. 1-30)
$[\alpha]_D^{20}$ -32.5° (c=1.0, methanol)
IR (film, cm$^{-1}$) 3368, 2958, 1736, 1650, 1511, 1455, 1386, 1174, 753, 698.

Benzyl(2S)-3-(4-biphenylyl)-2-[3-(2-diethoxyphosphonylethyl)-3-isobutylureido]propionate (compound No. 1-31)
$[\alpha]_D^{20}$ -18.5° (c=1.0, chloroform)
IR (film, cm$^{-1}$) 3349, 3030, 2959, 2358, 1741, 1644, 1520, 1487, 1408, 1388, 1368, 1186, 1028, 970, 759, 698.

Ethyl(2S)-3-(4-biphenylyl)-2-[3-(2-tert.-butoxycarbonylethyl)-3-isobutylureido]propionate (compound No. 1-32)

tert.-Butyl(2S)-3-(4-biphenylyl)-2-[3-(2-ethoxycarbonylethyl)-3-isobutylureido]propionate (compound No. 1-33)

Benzyl(2S)-2-[3-[(2RS)-2-benzyloxycarbonylpropyl]-3-isobutylureido]-3-(4-biphenylyl)propionate (compound No. 1-34)

tert.-Butyl(2S)-3-(4-biphenylyl)-2-[3-[(2RS)-2-ethoxycarbonyl-5-methylhexyl]-3-isobutylureido]propionate (compound No. 1-35)

Benzyl(2S)-2-[3-[(2RS)-2-benzyloxycarbonyl-2-methoxyethyl]-3-isobutylureido]-3-(4-biphenylyl)propionate (compound No. 1-36)

Benzyl(2S)-2-[3-[(2RS)-2-benzyloxycarbonyl-2-isobutoxyethyl]-3-isobutylureido]-3-(4-biphenylyl)propionate (compound No. 1-37)

tert.-Butyl(2S)-3-(4-biphenylyl)-2-[3-[(2RS)-2-ethoxycarbonyl-3-phenylpropyl]-3-isobutylureido]propionate (compound No. 1-38)

Ethyl(2S)-3-(4-biphenylyl)-2-[3-[(2RS)-2-tert.-butoxycarbonyl-4-phenylbutyl]-3-isobutylureido]propionate (compound No. 1-39)

Ethyl(2S)-2-[3-[(2RS)-2-benzyloxycarbonyl-4-phenylbutyl]-3-isobutylureido]-3-(4-biphenylyl)propionate (compound No. 1-40)

tert.-Butyl(2S)-3-(4-biphenylyl)-2-[3-[(2RS)-2-ethoxycarbonyl-4-phenylbutyl]-3-isobutylureido]propionate (compound No. 1-41)

tert.-Butyl(2S)-2-[3-[(2RS)-2-benzyloxycarbonyl-4-phenylbutyl]-3-isobutylureido]-3-(4-biphenylyl)propionate (compound No. 1-42)

Benzyl(2S)-2-[3-(2-benzyloxycarbonylethyl)-3-isobutylureido]-3-[4-(4'-methyl-2-nitro)biphenylyl]propionate (compound No. 1-43)

Benzyl(2S)-2-[3-(2-benzyloxycarbonylethyl)-3-isobutylureido]-3-[4-(4'-hydroxy)biphenylyl]propionate (compound No. 1-44)

Benzyl(2S)-2-[3-(2-benzyloxycarbonylethyl)-3-isobutylureido]-3-[4-(4'-methoxy)biphenylyl]propionate (compound No. 1-45)

Benzyl(2S)-2-[3-(2-benzyloxycarbonylethyl)-3-isobutylureido]-3-[4-(4'-nitro)biphenylyl]propionate (compound No. 1-46)

Benzyl(2S)-2-[3-(2-benzyloxycarbonylethyl)-3-isobutylureido]-3-[4-(3'-nitro)biphenylyl]propionate (compound No. 1-47)

Benzyl(2S)-2-[3-[(2RS)-2-benzyloxycarbonyl-4-phenylbutyl]-3-isobutylureido]-3-[4-(4'-fluoro)biphenylyl]propionate (compound No. 1-48)

Benzyl(2S)-2-[3-[(2RS)-2-benzyloxycarbonyl-4-phenylbutyl]-3-isobutylureido]-3-[4-(4'-chloro)biphenylyl]propionate (compound No. 1-49)

Benzyl(2S)-2-[3-[(2RS)-2-benzyloxycarbonyl-4-phenylbutyl]-3-isobutylureido]-3-[4-(4'-methyl)biphenylyl]propionate (compound No. 1-50)

Benzyl(2S)-2-[3-[(2RS)-2-benzyloxycarbonyl-4-phenylbutyl]-3-isobutylureido]-3-[4-(4'-methyl-2-nitro)biphenylyl]propionate (compound No. 1-51)

Benzyl(2S)-2-[3-[(2RS)-2-benzyloxycarbonyl-4-phenylbutyl]-3-isobutylureido]-3-[4-(4'-hydroxy)biphenylyl]propionate (compound No. 1-52)

Benzyl(2S)-2-[3-[(2RS)-2-benzyloxycarbonyl-4-phenylbutyl]-3-isobutylureido]-3-[4-(4'-methoxy)biphenylyl]propionate (compound No. 1-53)

Benzyl(2S)-2-[3-[(2RS)-2-benzyloxycarbonyl-4-phenylbutyl]-3-isobutylureido]-3-[4-(3'-methoxy)biphenylyl]propionate (compound No. 1-54)

Benzyl(2S)-2-[3-[(2RS)-2-benzyloxycarbonyl-4-phenylbutyl]-3-isobutylureido]-3-[4-(2'-methoxy)biphenylyl]propionate (compound No. 1-55)

Benzyl(2S)-2-[3-[(2RS)-2-benzyloxycarbonyl-4-phenylbutyl]-3-isobutylureido]-3-[4-(4'-nitro)biphenylyl]propionate (compound No. 1-56)

Benzyl(2S)-2-[3-[(2RS)-2-benzyloxycarbonyl-4-phenylbutyl]-3-isobutylureido]-3-[4-(3'-nitro)biphenylyl]propionate (compound No. 1-57)

Benzyl(2S)-2-[3-[(2RS)-2-benzyloxycarbonyl-4-phenylbutyl]-3-isobutylureido]-3-[4-(2-nitro)biphenylyl]propionate (compound No. 1-58)

Benzyl(2RS)-2-[3-[(2RS)-2-benzyloxycarbonyl-4-phenylbutyl]-3-isobutylureido]-3-(3-biphenylyl)propionate (compound No. 1-59)

Benzyl(2S)-2-[3-[(2RS)-2-benzyloxycarbonyl-4-phenylbutyl]-3-isobutylureido]-3-(1,1':4',1''-terphenyl-4-yl)propionate (compound No. 1-60)

Benzyl(2S)-2-[3-[(2RS)-2-benzyloxycarbonyl-4-phenylbutyl]-3-isobutylureido]-3-(1,1':2',1''-terphenyl-4-yl)propionate (compound No. 1-61)

Benzyl(2S)-2-[3-[(2RS)-2-benzyloxycarbonyl-4-phenylbutyl]-3-isobutylureido]-3-[4-(2-naphthyl)phenyl]propionate (compound No. 1-62)

Benzyl(2S)-2-[3-[(2RS)-2-benzyloxycarbonyl-4-phenylbutyl]-3-isobutylureido]-3-[4-(1-naphthyl)phenyl]propionate (compound No. 1-63)

tert.-Butyl(2S)-2-[3-[(2RS)-2-ethoxycarbonyl-4-phenylbutyl]-3-isobutylureido]-3-(2-naphthyl)propionate (compound No. 1-64)

Methyl(2S)-2-[3-[(2RS)-2-benzyloxycarbonyl-4-phenylbutyl]-3-isobutylureido]-3-[2-(1-bromo)naphthyl]propionate (compound No. 1-65)

Benzyl(2S)-2-[3-[(2RS)-2-benzyloxycarbonyl-4-phenylbutyl]-3-isobutylureido]-3-[2-(6-methoxy)naphthyl]propionate (compound No. 1-66)

Benzyl(2S)-2-[3-[(2RS)-2-benzyloxycarbonyl-4-phenylbutyl]-3-isobutylureido]-3-(1-naphthyl)propionate (compound No. 1-67)

Benzyl(2S)-2-[3-[(2RS)-2-benzyloxycarbonyl-4-phenylbutyl]-3-methylureido]-3-(4-biphenylyl)propionate (compound No. 1-68)

Benzyl(2S)-2-[3-[(2RS)-2-benzyloxycarbonyl-4-phenylbutyl]-3-methylureido]-3-(2-naphthyl)propionate (compound No. 1-69)

Benzyl(2S)-2-[3-benzyl-3-[(2RS)-2-benzyloxycarbonyl-4-phenylbutyl]ureido]-3-(4-biphenylyl)propionate (compound No. 1-70)

Benzyl(2S)-2-[3-benzyl-3-[(2RS)-2-benzyloxycarbonyl-4-phenylbutyl]ureido]-3-(2-naphthyl)propionate (compound No. 1-71)

Benzyl(2S)-3-(4-biphenylyl)-2-[3-(2-carbamoylethyl)-3-isobutylureido]propionate (compound No. 1-72)

(2S)-2-[3-(2-Benzyloxycarbonylethyl)-3-isobutylureido]-3-(4-biphenylyl)propionamide (compound No. 1-73)

(2S)-3-(4-Biphenylyl)-2-[3-(2-carbamoylethyl)-3-isobutylureido]propionamide (compound No. 1-74)

Benzyl(2S)-3-(4-biphenylyl)-2-[3-[(2RS)-2-carbamoyl-5-methylhexyl]-3-isobutylureido]propionate (compound No. 1-75)

Benzyl(2S)-3-(4-biphenylyl)-2-[3-[(2RS)-2-carbamoyl-3-phenylpropyl]-3-isobutylureido]propionate (compound No. 1-76)

Benzyl(2S)-3-(4-biphenylyl)-2-[3-[(2RS)-2-carbamoyl-4-phenylbutyl]-3-isobutylureido]propionate (compound No. 1-77)

(2S)-2-[3-[(2RS)-2-Benzyloxycarbonyl-4-phenylbutyl]-3-isobutylureido]-3-(4-biphenylyl)propionamide (compound No. 1-78)

(2S)-3-(4-Biphenylyl)-2-[3-[(2RS)-2-carbamoyl-4-phenylbutyl]-3-isobutylureido]propionamide (compound No. 1-79)

Benzyl(2S)-2-[3-[(2RS)-2-benzyloxy-2-carbamoylethyl]-3-isobutylureido]-3-(4-biphenylyl)propionate (compound No. 1-80)

Benzyl(2S)-2-[3-[(2RS)-2-carbamoyl-4-phenylbutyl]-3-isobutylureido]-3-(2-naphthyl)propionate (compound No. 1-81)

Benzyl(2S)-3-(4-biphenylyl)-2-[3-(2-diethoxyphosphonylethyl)-3-isobutylureido]propionate (compound No. 1-82)

Benzyl(2S)-3-(4-biphenylyl)-2-[3-isobutyl-3-(2-isopropyloxycarbonylethyl)ureido]propionate (compound No. 1-83)

$[\alpha]_D^{20}$ −21.4° (c=0.99, chloroform)

IR (film, cm$^{-1}$) 3391, 3030, 2959, 2871, 1732, 1651, 1519, 1186, 1108, 760, 697.

Benzyl(2S)-3-(4-biphenylyl)-2-[3-[(2S or 2R)-2-tert.-butoxycarbonyl-4-phenylbutyl]-3-isobutylureido]propionate (compound No. 1-84)

Single diastereomer of compound No. 1-7

Diastereomer of compound No. 1-85

$[\alpha]_D^{20}$ −20.8° (c=1.0, methanol)

IR (film, cm$^{-1}$) 3448, 3028, 2959, 1723, 1651, 1367, 756, 698.

Benzyl(2S)-3-(4-biphenylyl)-2-[3-[(2R or 2S)-2-tert.-butoxycarbonyl-4-phenylbutyl]-3-isobutylureido]propionate (compound No. 1-85)
Single diastereomer of compound No. 1-7
Diastereomer of compound No. 1-84
$[\alpha]_D^{20}$ −17.6° (C=1.0, methanol)
IR (film, cm$^{-1}$) 3450, 3028, 2959, 1723, 1651, 1512, 1367, 757, 698.
Benzyl(2S)-2-[3-(2-tert.-butoxycarbonylethyl)-3-isobutylureido]-3-(2-naphthyl)propionate (compound No. 1-86)
$[\alpha]_D^{20}$ −27.9° (c=1.0, chloroform)
IR (film, cm$^{-1}$) 3441, 3293, 3053, 3007, 1731, 1623, 1528, 1495, 1387, 827, 753.
Benzyl(2S)-2-[3-[(2S or 2R)-2-tert.-butoxycarbonyl-4-phenylbutyl]-3-isobutylureido]-3-(2-naphthyl)propionate (compound No. 1-87)
Single diastereomer of compound No. 1-26
Diastereomer of compound No. 1-88
$[\alpha]_D^{20}$ −15.2° (c=1.1, chloroform)
IR (film, cm$^{-1}$) 3449, 3364, 2960, 1723, 1650, 1511, 1455, 1367, 1151, 751, 699.
Benzyl(2S)-2-[3-[(2R or 2S)-2-tert.-butoxycarbonyl-4-phenylbutyl]-3-isobutylureido]-3-(2-naphthyl)propionate (compound No. 1-88)
Single diastereomer of compound No. 1-26
Diastereomer of compound No. 1-87
$[\alpha]_D^{20}$ −26.7° (c=0.99, chloroform)
IR (film, cm$^{-1}$) 3350, 2958, 1722, 1654, 1508, 1454, 1367, 1152, 748, 699.

EXAMPLE 2 tert.-Butyl(2S)-3-(4-biphenylyl)-2-[3-(2-hydroxycarbamoylethyl)-3-isobutylureido]propionate (compound No. 2-1)

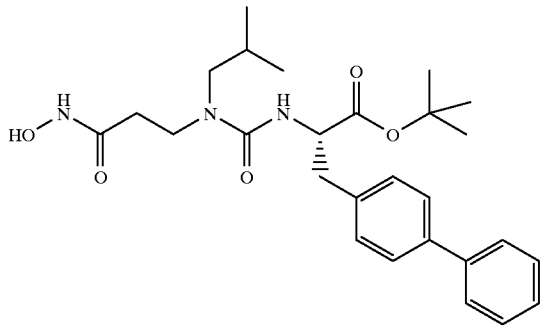

To a solution of hydroxyammonium chloride (1.34 g) in methanol (33 ml) is added 28% sodium methoxide/methanol (7.4 ml). The mixture is stirred at room temperature for five minutes. The reaction mixture is added to a solution of tert.-butyl(2S)-3-(4-biphenylyl)-2-[3-(2-ethoxycarbonylethyl)-3-isobutylureido]propionate (compound No. 1-33, 7.7 g) in methanol (66 ml) under ice-cooling. The mixture is stirred under ice-cooling for 15 minutes and further at room temperature overnight. To the reaction mixture is added a 10% aqueous citric acid solution to adjust pH to 5. The resulting mixture is concentrated in vacuo to remove methanol. The obtained solution is extracted with ethyl acetate. The organic layer is washed with a saturated sodium chloride solution, dried over magnesium sulfate and concentrated in vacuo. The oily residue is purified by silica gel column chromatography to give the titled compound (compound No. 2-1).

The following compounds can be prepared by a method similar to Example 2.
(2S)-3-(4-Biphenylyl)-2-[3-(2-tert.-butoxycarbonylethyl)-3-isobutylureido]propionohydroxamic acid (compound No. 2-2)
(2S)-3-(4-Biphenylyl)-2-[3-(2-hydroxycarbamoylethyl)-3-isobutylureido]propionohydroxamic acid (compound No. 2-3)
tert.-Butyl(2S)-3-(4-biphenylyl)-2-[3-[(2RS)-2-hydroxycarbamoyl-5-methylhexyl]-3-isobutylureido]propionate (compound No. 2-4)
tert.-Butyl(2S)-3-(4-biphenylyl)-2-[3-[(2RS)-2-hydroxycarbamoyl-3-phenylbutyl]-3-isobutylureido]propionate (compound No. 2-5)
tert.-Butyl(2S)-3-(4-biphenylyl)-2-[3-[(2RS)-2-hydroxycarbamoyl-4-phenylbutyl]-3-isobutylureido]propionate (compound No. 2-6)
(2S)-3-(4-Biphenylyl)-2-[3-[(2RS)-2-tert.-butoxycarbonyl-4-phenylbutyl]-3-isobutylureido]propionohydroxamic acid (compound No. 2-7)
(2S)-3-(4-Biphenylyl)-2-[3-[(2RS)-2-hydroxycarbamoyl-4-phenylbutyl]-3-isobutylureido]propionohydroxamic acid (compound No. 2-8)
tert.-Butyl(2S)-2-[3-[(2RS)-2-benzyloxy-2-hydroxycarbamoylethyl]-3-isobutylureido]-3-(4-biphenylyl)propionate (compound No. 2-9)
tert.-Butyl(2S)-2-[3-[(2RS)-2-hydroxycarbamoyl-4-phenylbutyl]-3-isobutylureido]-3-(2-naphthyl)propionate (compound No. 2-10)

EXAMPLE 3

Benzyl(2S)-3-(4-biphenylyl)-2-[3-(2-carboxyethyl)-3-isobutylureido]propionate (compound No. 3-1)

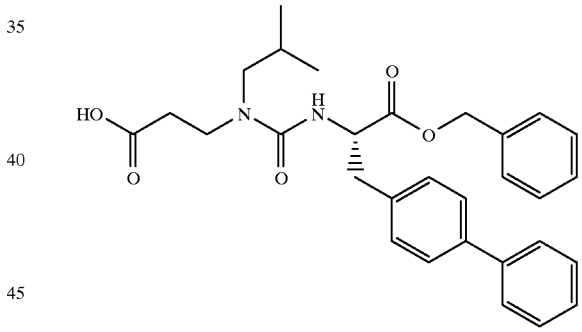

To benzyl(2S)-3-(4-biphenylyl)-2-[3-(2-tert.-butoxycarbonylethyl)-3-isobutylureido]propionate (compound No. 1-2, 7.84 g) is added 4.0 N hydrochloric acid/dioxane (35 ml). The mixture is stirred at room temperature for 3.5 hours. The reaction mixture is concentrated in vacuo. The oily residue is purified by silica gel column chromatography to give 6.12 g (87%) of the titled compound (compound No. 3-1) as amorphous powder.
$[\alpha]_D^{20}$ −28.0° (c=0.98, methanol)
IR (film, cm$^{-1}$) 3029, 2959, 1731, 1615, 1523, 1487, 1451, 1190.
The following compounds can be prepared by a method similar to Example 3.
Benzyl(2S)-3-(4-biphenylyl)-2-[3-[(2RS)-2-carboxy-4-phenylbutyl]-3-isobutylureido]propionate (compound No. 3-2)
$[\alpha]_D^{20}$ −24.6° (c=1.0, methanol)
IR (film, cm$^{-1}$) 3445, 2958, 1732, 1614, 1519, 1455, 1190, 758, 698.

Benzyl(2S)-2-[3-[(2RS)-2-carboxy-4-phenylbutyl]-3-isobutylureido]-3-(2-naphthyl)propionate (compound No. 3-3)
[α]$_D^{20}$ −27.0° (c=0.49, chloroform)
IR (film, cm$^{-1}$) 3441, 2958, 1734, 1617, 1522, 1454, 1190, 751, 699.

(2S)-3-(4-Biphenylyl)-2-[3-(2-phosphonylethyl)-3-isobutylureido]propionic acid (compound No. 3-4)
[α]$_D^{20}$ −23.6° (c=0.38, dimethyl sulfoxide)
IR (KBr, cm$^{-1}$) 3384, 2959, 1736, 1695, 1602, 1538, 1488, 1248, 1152, 1008, 940, 761, 689.

Benzyl(2S)-3-(4-biphenylyl)-2-[3-[(2RS)-2-carboxy-5-methylhexyl]-3-isobutylureido]propionate (compound No. 3-5)

Benzyl(2S)-3-(4-biphenylyl)-2-[3-[(2RS)-2-carboxy-3-phenylpropyl]-3-isobutylureido]propionate (compound No. 3-6)

(2S)-3-(4-Biphenylyl)-2-[3-[(2RS)-2-benzyloxycarbonyl-4-phenylbutyl]-3-isobutylureido]propionic acid (compound No. 3-7)

Benzyl(2S)-3-(4-biphenylyl)-2-[3-[(2RS)-2-carboxy-5-phenylpentyl]-3-isobutylureido]propionate (compound No. 3-8)

Benzyl(2S)-3-(4-biphenylyl)-2-[3-[(2RS)-2-carboxy-6-phenylhexyl]-3-isobutylureido]propionate (compound No. 3-9)

(2S)-3-(4-Biphenylyl)-2-[3-(2-hydroxycarbamoylethyl)-3-isobutylureido]propionic acid (compound No. 3-10)

(2S)-3-(4-Biphenylyl)-2-[3-(2-carboxyethyl)-3-isobutylureido]propionohydroxamic acid (compound No. 3-11)

(2S)-3-(4-Biphenylyl)-2-[3-[(2RS)-2-hydroxycarbamoyl-5-methylhexyl]-3-isobutylureido]propionic acid (compound No. 3-12)

(2S)-3-(4-Biphenylyl)-2-[3-[(2RS)-2-hydroxycarbamoyl-3-phenylpropyl)-3-isobutylureido]propionic acid (compound No. 3-13)

(2S)-3-(4-Biphenylyl)-2-[3-[(2RS)-2-hydroxycarbamoyl-4-phenylbutyl)-3-isobutylureido]propionic acid (compound No. 3-14)

(2S)-3-(4-Biphenylyl)-2-[3-[(2RS)-2-carboxy-4-phenylbutyl]-3-isobutylureido]propionohydroxamic acid (compound No. 3-15)

(2S)-2-[3-[(2RS)-2-Benzyloxy-2-hydroxycarbamoylethyl]-3-isobutylureido]-3-(4-biphenylyl)propionic acid (compound No. 3-16)

(2S)-2-[3-[(2RS)-2-Hydroxycarbamoyl-4-phenylbutyl]-3-isobutylureido]-3-(2-naphthyl)propionic acid (compound No. 3-17)

(2S)-2-[3-(2-Phosphonylethyl)-3-isobutylureido]-3-(2-naphthyl)propionic acid (compound No. 3-18)

Benzyl(2S)-3-(4-biphenylyl)-2-[3-[(2S or 2R)-2-carboxy-4-phenylbutyl]-3-isobutylureido]propionate (compound No. 3-19)
Single diastereomer of compound No. 3-2
Diastereomer of compound No. 3-20
[α]$_D^{20}$ −21.1° (c=0.36, methanol)
IR (film, cm$^{-1}$) 3445, 2958, 1732, 1617, 1519, 1387, 1345, 1190, 758, 698.

Benzyl(2S)-3-(4-biphenylyl)-2-[3-[(2R or 2S)-2-carboxy-4-phenylbutyl]-3-isobutylureido]propionate (compound No. 3-20)
Single diastereomer of compound No. 3-2
Diastereomer of compound No. 3-19

(2S)-2-[3-(2-Carboxyethyl)-3-isobutylureido]-3-(2-naphthyl)propionic acid (compound No. 3-21)
[α]$_D^{20}$ −33.7° (c=1.0, chloroform)
mp 102.5–104.5° C.
IR (KBr, cm$^{-1}$) 3379, 2960, 1741, 1609, 1533, 1365, 1272, 1077, 953, 817, 782, 746, 695.

Benzyl(2S)-2-[3-[(2S or 2R)-2-carboxy-4-phenylbutyl]-3-isobutylureido]-3-(2-naphthyl)propionate (compound No. 3-22)
Single diastereomer of compound No. 3-3
Single diastereomer of compound No. 3-23
[α]$_D^{20}$ −22.8° (c=1.0, chloroform)
IR (film, cm$^{-1}$) 3445, 3027, 2958, 1732, 1615, 1524, 1455, 1190, 751, 699.

Benzyl(2S)-2-[3-[(2R or 2S)-2-carboxy-4-phenylbutyl]-3-isobutylureido]-3-(2-naphthyl)propionate (compound No. 3-23)
Single diastereomer of compound No. 3-3
Single diastereomer of compound No. 3-22

Benzyl(2S)-2-[3-[(2S or 2R)-2-butoxycarbonyl-4-phenylbutyl]-3-isobutylureido]-3-(2-naphthyl)propionate (compound No. 3-24)
[α]$_D^{20}$ −22.3° (c=1.0, chloroform)
IR (film, cm$^{-1}$) 3447, 3061, 3027, 2958, 2871, 1732, 1615, 1509, 1372, 1180, 746, 699.

EXAMPLE 4

Benzyl(2S)-2-[3-[2-(2-acetamidoethoxycarbonyl)ethyl]-3-isobutylureido]-3-(4-biphenylyl)propionate (compound No. 4-1)

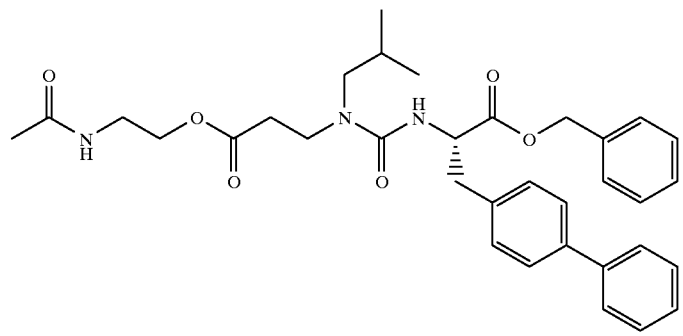

To a solution of benzyl(2S)-3-(4-biphenylyl)-2-[3-(2-carboxyethyl)-3-isobutylureido]propionate (compound No. 3-1, 1.35 g), 2-acetamidoethanol (291 mg) and 4-dimethylaminopyridine (164 mg) in dichloromethane (7 ml) is added a solution of dicyclohexylcarbodiimide (665 mg) in dichloromethane (6 ml) under ice-cooling. The mixture is stirred for 30 minutes. After the reaction mixture is further stirred at room temperature for 24 hours, a precipitated insoluble matter is removed by filtration, and the filtrate is concentrated in vacuo. The oily residue is purified by silica gel column chromatography to give 1.29 g (82%) of the titled compound (compound No. 4-1).

$[\alpha]_D^{20}$ −21.1° (c=1.2, methanol)

IR (film, cm$^{-1}$) 3308, 2959, 1735, 1636, 1521, 1279, 1177, 756, 698.

The following compounds can be prepared by a method similar to Example 4.

Benzyl(2S)-3-(4-biphenylyl)-2-[3-isobutyl-3-[2-(2-methoxyphenoxycarbonyl)ethyl]ureido]propionate (compound No. 4-2)

$[\alpha]_D^{20}$ −28.1° (c=1.0, methanol)

IR (film, cm$^{-1}$) 3367, 3029, 2958, 2871, 2839, 1746, 1651, 1607, 1501, 1464.

Benzyl(2S)-3-(4-biphenylyl)-2-[3-[2-(5-indanyloxycarbonyl)ethyl]-3-isobutylureido]propionate (compound No. 4-3)

$[\alpha]_D^{20}$ −27.6° (c=1.0, methanol)

IR (film, cm$^{-1}$) 3368, 2957, 1748, 1648, 1513, 1145, 758, 698.

Benzyl(2S)-2-[3-[(2RS)-2-(2-acetamidoethoxycarbonyl)-4-phenylbutyl]-3-isobutylureido]-3-(4-biphenylyl)propionate (compound No. 4-4)

$[\alpha]_D^{20}$ −20.4° (c=1.0, methanol)

IR (film, cm$^{-1}$) 3305, 2957, 1732, 1634, 1519, 1455, 1260, 1171, 756, 698.

Benzyl(2S)-3-(4-biphenylyl)-2-[3-isobutyl-3-[(2RS)-2-(2-methoxyphenoxycarbonyl)-4-phenylbutyl]ureido]propionate (compound No. 4-5)

$[\alpha]_D^{20}$ −25.6° (c=0.53, methanol)

IR (film, cm$^{-1}$) 3449, 3062, 3028, 2957, 1749, 1651, 1500, 1455, 1258.

Benzyl(2S)-3-(4-biphenylyl)-2-[3-[(2RS)-2-(5-indanyloxycarbonyl)-4-phenylbutyl]-3-isobutylureido]propionate (compound No. 4-6)

$[\alpha]_D^{20}$ −24.0° (c=0.97, methanol)

IR (film, cm$^{-1}$) 3448, 3061, 2956, 1746, 1650, 1513, 1142, 756, 698.

2-Acetamidoethyl(2S)-2-[3-(2-benzyloxycarbonylethyl)-3-isobutylureido]-3-(4-biphenylyl)propionate (compound No. 4-7)

2-Methoxyphenyl(2S)-2-[3-(2-benzyloxycarbonylethyl)-3-isobutylureido]-3-(4-biphenylyl)propionate (compound No. 4-8)

5-Indanyl(2S)-2-[3-(2-benzyloxycarbonylethyl)-3-isobutylureido]-3-(4-biphenylyl)propionate (compound No. 4-9)

Benzyl(2S)-2-[3-[(2RS)-2-(2-acetamidoethoxycarbonyl)-5-methylhexyl]-3-isobutylureido]-3-(4-biphenylyl)propionate (compound No. 4-10)

Benzyl(2S)-3-(4-biphenylyl)-2-[3-isobutyl-3-[(2RS)-2-(2-methoxyphenoxycarbonyl)-5-methylhexyl]ureido]propionate (compound No. 4-11)

Benzyl(2S)-3-(4-biphenylyl)-2-[3-[(2RS)-2-(5-indanyloxycarbonyl)-5-methylhexyl]-3-isobutylureido]propionate (compound No. 4-12)

Benzyl(2S)-2-[3-[(2RS)-2-(2-acetamidoethoxycarbonyl)-3-phenylpropyl]-3-isobutylureido]-3-(4-biphenylyl)propionate (compound No. 4-13)

Benzyl(2S)-3-(4-biphenylyl)-2-13-isobutyl-3-[(2RS)-2-(2-methoxyphenoxycarbonyl)-3-phenylpropyl]ureido]propionate (compound No. 4-14)

Benzyl(2S)-3-(4-biphenylyl)-2-[3-[(2RS)-2-(5-indanyloxycarbonyl)-3-phenylpropyl]-3-isobutylureido]propionate (compound No. 4-15)

2-Acetamidoethyl(2S)-2-[3-[(2RS)-2-benzyloxycarbonyl-4-phenylbutyl]-3-isobutylureido]-3-(4-biphenylyl)propionate (compound No. 4-16)

2-Methoxyphenyl(2S)-2-[3-[(2RS)-2-benzyloxycarbonyl-4-phenylbutyl]-3-isobutylureido]-3-(4-biphenylyl)propionate (compound No. 4-17)

5-Indanyl(2S)-2-[3-[(2RS)-2-benzyloxycarbonyl-4-phenylbutyl]-3-isobutylureido]-3-(4-biphenylyl)propionate (compound No. 4-18)

Benzyl(2S)-2-[3-[(2RS)-2-(2-acetamidoethoxycarbonyl)-2-benzyloxyethyl]-3-isobutylureido]-3-(4-biphenylyl)propionate (compound No. 4-19)

Benzyl(2S)-2-[3-[(2RS)-2-benzyloxy-2-(2-methoxyphenoxycarbonyl)ethyl]-3-isobutylureido]-3-(4-biphenylyl)propionate (compound No. 4-20)

Benzyl(2S)-2-[3-[(2RS)-2-benzyloxy-2-(5-indanyloxycarbonyl)ethyl]-3-isobutylureido]-3-(4-biphenylyl)propionate (compound No. 4-21)

Benzyl(2S)-2-[3-[(2RS)-2-(2-acetamidoethoxycarbonyl)-4-phenylbutyl]-3-isobutylureido]-3-(2-naphthyl)propionate (compound No. 4-22)

Benzyl(2S)-2-[3-isobutyl-3-[(2RS)-2-(2-methoxyphenoxycarbonyl)-4-phenylbutyl]ureido]-3-(2-naphthyl)propionate (compound No. 4-23)

Benzyl(2S)-2-[3-[(2RS)-2-(5-indanyloxycarbonyl)-4-phenylbutyl]-3-isobutylureido]-3-(2-naphthyl)propionate (compound No. 4-24)

Benzyl(2S)-3-(4-biphenylyl)-2-[3-(2-methoxycarbonylethyl)-3-isobutylureido]propionate (compound No. 4-25)

$[\alpha]_D^{20}$ −24.7° (c=0.83, chloroform)

IR (film, cm$^{-1}$) 3350, 2956, 1737, 1645, 1519, 1438, 1257, 1175.

Benzyl(2S)-3-(4-biphenylyl)-2-[3-(2-butoxycarbonylethyl)-3-isobutylureido]propionate (compound No. 4-26)

mp 43.5–46.9° C. (decomp.)

$[\alpha]_D^{20}$ −21.6° (c=1.0, chloroform)

IR (film, cm$^{-1}$) 3350, 3030, 2958, 1732, 1644, 1519, 1487, 1178, 1008, 758, 697.

Benzyl(2S)-2-[3-(2-isobutoxycarbonylethyl)-3-isobutylureido]-3-(4-biphenylyl)propionate (compound No. 4-27)

$[\alpha]_D^{20}$ −20.6° (c=0.98, chloroform)

IR (film, cm$^{-1}$) 3349, 2959, 1733, 1652, 1517, 1467, 1382, 1186.

Benzyl(2S)-2-[3-[2-(4-acetamido)phenoxycarbonylethyl]-3-isobutylureido]-3-(4-biphenylyl)propionate (compound No. 4-28)

$[\alpha]_D^{20}$ −19.2° (c=0.18, chloroform)

IR (film, cm$^{-1}$) 3308, 2960, 1745, 1672, 1633, 1537, 1507, 1408, 1194, 757.

Benzyl(2S)-2-[3-(2-butoxycarbonylethyl)-3-isobutylureido]-3-(2-naphthyl)propionate (compound No. 4-29)

$[\alpha]_D^{20}$ −29.9° (c=1.0, chloroform)

IR (film, cm$^{-1}$) 3355, 3056, 2959, 1733, 1647, 1514, 1184, 818, 747, 699.

Benzyl(2S)-2-[3-[(2S or 2R)-2-ethoxycarbonyl-4-phenylbutyl]-3-isobutylureido]-3-(2-naphthyl)propionate (compound No. 4-30)

Single diastereomer of compound No. 1-25

Diastereomer of compound No. 4-31

$[\alpha]_D^{20}$ −23.9° (c=0.97, chloroform)

IR (film, cm$^{-1}$) 3445, 3373, 2957, 1867, 1729, 1653, 1507, 1253, 1185, 746, 698.

Benzyl(2S)-2-[3-[(2R or 2S)-2-ethoxycarbonyl-4-phenylbutyl]-3-isobutylureido]-3-(2-naphthyl)propionate (compound No. 4-31)
Single diastereomer of compound No. 1-25
Diastereomer of compound No. 4-30
4-Acetamidophenyl(2S)-2-[3-[(2S or 2R)-2-ethoxycarbonyl-4-phenylbutyl]-3-isobutylureido]-3-(2-naphthyl)propionate (compound No. 4-32)
mp 130° C.
$[\alpha]_D^{20}$ −37.3° (c=0.46, methanol)
IR (KBr, cm$^{-1}$) 3363, 3302, 2960, 1761, 1730, 1674, 1626, 1539, 1506, 1454, 1268, 1195.

EXAMPLE 5

(2S)-3-(4-Biphenylyl)-2-[3-(2-carboxyethyl)-3-isobutylureido]propionic acid (compound No. 5-1)

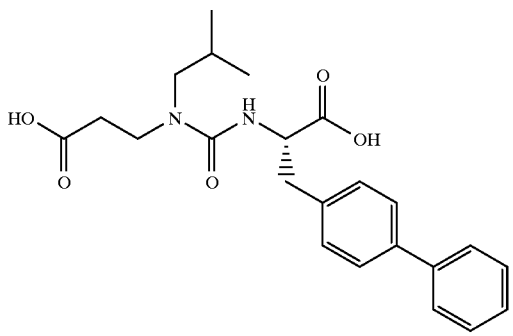

To a solution of benzyl(2S)-2-[3-(2-benzyloxycarbonylethyl)-3-isobutylureido]-3-(4-biphenylyl)propionate (compound No. 1-3, 270 mg) in methanol (5 ml) is added 5% palladium on carbon (50 mg) under a nitrogen atmosphere. The mixture is stirred under a hydrogen atmosphere for 1.5 hours. The palladium on carbon is removed by Celite filtration, and the filtrate is concentrated in vacuo. The oily residue is purified by silica gel column chromatography to give 90 mg (48.4%) of the titled compound (compound No. 5-1).

mp 131–133° C. (decomp.)
$[\alpha]_D^{20}$ −11.9° (c=1.0, methanol)
IR (KBr, cm$^{-1}$) 3435, 2958, 1720, 1592, 1526, 1488, 1278, 1240, 764.

The following compounds can be prepared by a method similar to Example 5.
(2S)-3-(4-Biphenylyl)-2-[3-(2-ethoxycarbonylethyl)-3-isobutylureido]propionic acid (compound No. 5-2)
mp 76.5–81.8° C. (diethyl ether-hexane)
$[\alpha]_D^{20}$ −11.9° (c=0.99, methanol)
IR (KBr, cm$^{-1}$) 3391, 2965, 1720, 1634, 1523, 1489, 1447, 1190.
(2S)-2-[3-[2-(2-Acetamidoethoxycarbonyl)ethyl]-3-isobutylureido]-3-(4-biphenylyl)propionic acid (compound No. 5-3)
mp 60.5–71.5° C. (hexane-ethyl acetate)
$[\alpha]_D^{20}$ −9.5° (c=1.0, chloroform)
IR (KBr, cm$^{-1}$) 3392, 2958, 1735, 1709, 1658, 1631, 1537, 1489, 1179, 762, 698.
(2S)-3-(4-Biphenylyl)-2-[3-isobutyl-3-[2-(2-methoxyphenoxycarbonyl)ethyl]ureido]propionic acid (compound No. 5-4)
$[\alpha]_D^{20}$ −33.3° (c=0.99, chloroform)
IR (KBr, cm$^{-1}$) 3435, 2958, 1761, 1607, 1501, 1465, 1310, 1258.
(2S)-3-(4-Biphenylyl)-2-[3-[2-(5-indanyloxycarbonyl)ethyl]-3-isobutylureido]propionic acid (compound No. 5-5)
$[\alpha]_D^{20}$ −24.5° (c=1.0, chloroform)
IR (KBr, cm$^{-1}$) 3435, 2958, 1754, 1610, 1524, 1145, 757, 697.
(2S)-3-(4-Biphenylyl)-2-[3-[(2RS)-2-carboxy-4-phenylbutyl]-3-isobutylureido]propionic acid (compound No. 5-6)
$[\alpha]_D^{20}$ −43.5° (c=0.26, chloroform)
IR (KBr, cm$^{-1}$) 2957, 1734, 1602, 1522, 1452, 1203, 756, 697.
(2S)-3-(4-Biphenylyl)-2-[3-[(2RS)-2-ethoxycarbonyl-4-phenylbutyl]-3-isobutylureido]propionic acid (compound No. 5-7)
$[\alpha]_D^{20}$ 4.0° (c=1.0, methanol)
IR (film, cm$^{-1}$) 3435, 2957, 2870, 1727, 1612, 1520, 1454, 1199, 756, 699.
(2S)-2-[3-[(2RS)-2-(2-Acetamidoethoxycarbonyl)-4-phenylbutyl]-3-isobutylureido]-3-(4-biphenylyl)propionic acid (compound No. 5-8)
$[\alpha]_D^{20}$ −7.5° (c=1.0, chloroform)
IR (KBr, cm$^{-1}$) 3305, 2958, 1733, 1628, 1519, 1454, 1197, 757, 698.
(2S)-3-(4-Biphenylyl)-2-[3-isobutyl-3-[(2RS)-2-(2-methoxyphenoxycarbonyl)-4-phenylbutyl]ureido]propionic acid (compound No. 5-9)
$[\alpha]_D^{20}$ −34.3° (c=1.0, chloroform)
IR (KBr, cm$^{-1}$) 3435, 3027, 2958, 1754, 1609, 1500, 1258, 1195, 1172, 1135, 1110.
(2S)-3-(4-Biphenylyl)-2-[3-[(2RS)-2-(5-indanyloxycarbonyl)-4-phenylbutyl]-3-isobutylureido]propionic acid (compound No. 5-10)
$[\alpha]_D^{20}$ −20.8° (c=1.0, chloroform)
IR (KBr, cm$^{-1}$) 3436, 3027, 2956, 1748, 1608, 1520, 1142, 755, 698.
(2S)-3-(4-Biphenylyl)-2-[3-[(2RS)-2-carboxy-5-phenylpentyl]-3-isobutylureido]propionic acid (compound No. 5-11)
$[\alpha]_D^{20}$ −39.7° (c=1.0, chloroform)
IR (KBr, cm$^{-1}$) 3435, 2959, 1726, 1603, 1523, 1487, 1203, 756, 698.
(2S)-3-(4-Biphenylyl)-2-[3-[(2RS)-2-carboxy-6-phenylhexyl]-3-isobutylureido]propionic acid (compound No. 5-12)
$[\alpha]_D^{20}$ −39.8° (c=0.97, chloroform)
IR (KBr, cm$^{-1}$) 3435, 2933, 1728, 1603, 1526, 1487, 1201, 757, 698.
(2S)-2-[3-(2-Carboxyethyl)-3-isobutylureido]-3-[4-(4'-fluoro)biphenylyl]propionic acid (compound No. 5-13)
$[\alpha]_D^{20}$ −11.5° (c=0.52, methanol)
IR (film, cm$^{-1}$) 2960, 1722, 1604, 1526, 1498, 1224, 1159, 1076, 820, 757, 667.
(2S)-2-[3-(2-Carboxyethyl)-3-isobutylureido]-3-[4-(4'-methyl)biphenylyl]propionic acid (compound No. 5-14)
mp 139.5–142.0° C. (decomp.)
$[\alpha]_D^{20}$ −30.3° (c=0.98, chloroform)
IR (KBr, cm$^{-1}$) 3442, 2959,1726, 1704,1591, 1529,1500, 1274, 804.
(2S)-2-[3-(2-Carboxyethyl)-3-isobutylureido]-3-[4-(3'-methoxy)biphenylyl]propionic acid (compound No. 5-15)
$[\alpha]_D^{20}$ −22.8° (c=1.0, chloroform)
IR (KBr, cm$^{-1}$) 2960, 1733, 1607, 1527, 1482, 1405, 1296, 1213.
(2S)-2-[3-(2-Carboxyethyl)-3-isobutylureido]-3-[4-(2'-methoxy)biphenylyl]propionic acid (compound No. 5-16)
$[\alpha]_D^{20}$ −15.4° (c=0.49, dimethyl sulfoxide)

IR (KBr, cm$^{-1}$) 2961, 1728, 1599, 1530, 1488, 1237, 1029.

(2RS)-3-(3-Biphenylyl)-2-[3-(2-carboxyethyl)-3-isobutylureido]propionic acid (compound No. 5-17)
IR (KBr, cm$^{-1}$) 2960, 1717, 1606, 1525, 1202, 810, 700.

(2S)-2-[3-(2-Carboxyethyl)-3-isobutylureido]-3-(1,1':2',1"-terphenyl-4-yl)propionic acid (compound No. 5-18)
$[\alpha]_D^{20}$ -3.1° (c=0.51, methanol)
IR (film, cm$^{-1}$) 3021, 2960, 1721, 1615, 1527, 1449, 1217, 759, 701.

(2S)-2-[3-(2-Carboxyethyl)-3-isobutylureido]-3-[4-(2-naphthyl)phenyl]propionic acid (compound No. 5-19)
$[\alpha]_D^{20}$ -34.5° (c=1.0, dimethyl sulfoxide)
IR (KBr, cm$^{-1}$) 2959, 1721, 1602, 1526, 1410, 1197, 813, 750.

(2S)-2-[3-(2-Carboxyethyl)-3-isobutylureido]-3-[4-(1-naphthyl)phenyl]propionic acid (compound No. 5-20)
mp 182.0° C. (decomp.)
$[\alpha]_D^{20}$ -47.3° (c=1.0, dimethyl sulfoxide)
IR (KBr, cm$^{-1}$) 3369, 2957, 1722, 1610, 1537, 1231, 1161, 898, 802, 776, 670.

(2S)-2-[3-(2-Carboxyethyl)-3-isobutylureido]-3-(2-naphthyl)propionic acid (compound No. 5-21)
mp 132.8–134.0° C.
$[\alpha]_D^{20}$ -24.5° (c=0.50, methanol)
IR (KBr, cm$^{-1}$) 3428, 2960, 1750, 1732, 1717, 1614, 1544, 1253, 1177.

(2S)-2-[3-(2-Carboxyethyl)-3-isobutylureido]-3-(1-naphthyl)propionic acid (compound No. 5-22)
mp 150.0–150.6° C. (decomp.)
$[\alpha]_D^{20}$ -71.9° (c=0.32, methanol)
IR (KBr, cm$^{-1}$) 3430, 1751, 1715, 1614, 1543, 1385, 1253, 1175.

2-Acetamidoethyl(2S)-3-(4-biphenylyl)-2-[3-(2-carboxyethyl)-3-isobutylureido]propionate (compound No. 5-23)

2-Methoxyphenyl(2S)-3-(4-biphenylyl)-2-[3-(2-carboxyethyl)-3-isobutylureido]propionate (compound No. 5-24)

5-Indanyl(2S)-3-(4-biphenylyl)-2-[3-(2-carboxyethyl)-3-isobutylureido]propionate (compound No. 5-25)

(2S)-2-[3-[(2RS)-2-(2-Acetamidoethoxycarbonyl)-5-methylhexyl]-3-isobutylureido]-3-(4-biphenylyl)propionic acid (compound No. 5-26)

(2S)-3-(4-Biphenylyl)-2-[3-isobutyl-3-[(2RS)-2-(2-methoxyphenoxycarbonyl)-5-methylhexyl]ureido]propionic acid (compound No. 5-27)

(2S)-3-(4-Biphenylyl)-2-[3-[(2RS)-2-(5-indanyloxycarbonyl)-5-methylhexyl]-3-isobutylureido]propionic acid (compound No. 5-28)

(2S)-3-(4-Biphenylyl)-2-[3-isobutyl-3-[(2RS)-2-methoxycarbonyl-4-phenylbutyl]ureido]propionic acid (compound No. 5-29)

(2S)-3-(4-Biphenylyl)-2-[3-[(2RS)-2-isobutoxycarbonyl-4-phenylbutyl]-3-isobutylureido]propionic acid (compound No. 5-30)

(2S)-2-[3-[(2RS)-2-(2-Acetamidoethoxycarbonyl)-3-phenylpropyl]-3-isobutylureido]-3-(4-biphenylyl)propionic acid (compound No. 5-31)

(2S)-3-(4-Biphenylyl)-2-[3-isobutyl-3-[(2RS)-2-(2-methoxyphenoxycarbonyl)-3-phenylpropyl]ureido]propionic acid (compound No. 5-32)

(2S)-3-(4-Biphenylyl)-2-[3-[(2RS)-2-(5-indanyloxycarbonyl)-3-phenylpropyl]-3-isobutylureido]propionic acid (compound No. 5-33)

Ethyl(2S)-3-(4-biphenylyl)-2-[3-[(2RS)-2-carboxy-4-phenylbutyl]-3-isobutylureido]propionate (compound No. 5-34)

2-Acetamidoethyl(2S)-3-(4-biphenylyl)-2-[3-[(2RS)-2-carboxy-4-phenylbutyl]-3-isobutylureido]propionate (compound No. 5-35)

2-Methoxyphenyl(2S)-3-(4-biphenylyl)-2-[3-[(2RS)-2-carboxy-4-phenylbutyl]-3-isobutylureido]propionate (compound No. 5-36)

5-Indanyl(2S)-3-(4-biphenylyl)-2-[3-[(2RS)-2-carboxy-4-phenylbutyl]-3-isobutylureido]propionate (compound No. 5-37)

(2S)-2-[3-(2-Carboxyethyl)-3-isobutylureido]-3-[4-(4'-hydroxy)biphenylyl]propionic acid (compound No. 5-38)

(2S)-2-[3-(2-Carboxyethyl)-3-isobutylureido]-3-[4-(4'-methoxy)biphenylyl]propionic acid (compound No. 5-39)

(2S)-3-[4-(4'-Amino)biphenylyl]-2-[3-(2-carboxyethyl)-3-isobutylureido]propionic acid (compound No. 5-40)

(2S)-2-[3-[(2RS)-2-Carboxy-4-phenylbutyl]-3-isobutylureido]-3-[4-(4'-fluoro)biphenylyl]propionic acid (compound No. 5-41)

(2S)-2-[3-[(2RS)-2-Carboxy-4-phenylbutyl]-3-isobutylureido]-3-[4-(4'-methyl)biphenylyl]propionic acid (compound No. 5-42)

(2S)-2-[3-[(2RS)-2-Carboxy-4-phenylbutyl]-3-isobutylureido]-3-[4-(4'-hydroxy)biphenylyl]propionic acid (compound No. 5-43)

(2S)-2-[3-[(2RS)-2-Carboxy-4-phenylbutyl]-3-isobutylureido]-3-[4-(4'-methoxy)biphenylyl]propionic acid (compound No. 5-44)

(2S)-2-[3-[(2RS)-2-Carboxy-4-phenylbutyl]-3-isobutylureido]-3-[4-(3'-methoxy)biphenylyl]propionic acid (compound No. 5-45)

(2S)-2-[3-[(2RS)-2-Carboxy-4-phenylbutyl]-3-isobutylureido]-3-[4-(2'-methoxy)biphenylyl]propionic acid (compound No. 5-46)

(2S)-3-[4-(4'-amino)biphenylyl]-2-[3-[(2RS)-2-carboxy-4-phenylbutyl]-3-isobutylureido]propionic acid (compound No. 5-47)

(2RS)-3-(3-Biphenylyl)-2-[3-[(2RS)-2-carboxy-4-phenylbutyl]-3-isobutylureido]propionic acid (compound No. 5-48)

(2S)-2-[3-[(2RS)-2-Carboxy-4-phenylbutyl]-3-isobutylureido]-3-(1,1':2', 1"-terphenyl-4-yl)propionic acid (compound No. 5-49)

(2S)-2-[3-[(2RS)-2-Carboxy-4-phenylbutyl]-3-isobutylureido]-3-[4-(2-naphthyl)phenyl]propionic acid (compound No. 5-50)

2(2S)-2-[3-[(2RS)-2-Carboxy-4-phenylbutyl]-3-isobutylureido]-3-[4-(1-naphthyl)phenyl]propionic acid (compound No. 5-51)

(2S)-2-[3-[(2RS)-2-(2-Acetamidoethoxycarbonyl)-4-phenylbutyl]-3-isobutylureido]-3-(2-naphthyl)propionic acid (compound No. 5-52)

(2S)-2-[3-Isobutyl-3-[(2RS)-2-(2-methoxyphenoxycarbonyl)-4-phenylbutyl]ureido]-3-(2-naphthyl)propionic acid (compound No. 5-53)

(2S)-2-[3-[(2RS)-2-(5-Indanyloxycarbonyl)-4-phenylbutyl]-3-isobutylureido]-3-(2-naphthyl)propionic acid (compound No. 5-54)

(2S)-2-[3-[(2RS)-2-Carboxy-4-phenylbutyl]-3-isobutylureido]-3-(1-naphthyl)propionic acid (compound No. 5-55)

(2S)-3-(4-Biphenylyl)-2-[3-[(2RS)-2-carboxy-4-phenylbutyl]-3-methylureido]propionic acid (compound No. 5-56)

(2S)-2-[3-[(2RS)-2-Carboxy-4-phenylbutyl]-3-methylureido]-3-(2-naphthyl)propionic acid (compound No. 5-57)

(2S)-3-(4-Biphenylyl)-2-[3-(2-carbamoylethyl)-3-isobutylureido]propionic acid (compound No. 5-58)

(2S)-3-(4-Biphenylyl)-2-[3-(2-carboxyethyl)-3-isobutylureido]propionamide (compound No. 5-59)

(2S)-3-(4-Biphenylyl)-2-[3-(2RS)-2-carbamoyl-5-methylhexyl]-3-isobutylureido]propionic acid (compound No. 5-60)

(2S)-3-(4-Biphenylyl)-2-[3-(2RS)-2-carbamoyl-3-phenylpropyl]-3-isobutylureido]propionic acid (compound No. 5-61)

(2S)-3-(4-Biphenylyl)-2-[3-(2RS)-2-carbamoyl-4-phenylbutyl]-3-isobutylureido]propionic acid (compound No. 5-62)

(2S)-3-(4-Biphenylyl)-2-[3-(2RS)-2-carboxy-4-phenylbutyl]-3-isobutylureido]propionamide (compound No. 5-63)

(2S)-2-[3-(2RS)-2-Carbamoyl-4-phenylbutyl]-3-isobutylureido]-3-(2-naphthyl)propionic acid (compound No. 5-64)

(2S)-3-(4-Biphenylyl)-2-[3-(2-diethoxyphosphonylethyl)-3-isobutylureido]propionic acid (compound No. 5-65)

(2S)-2-[3-(2-Diethoxyphosphonylethyl)-3-isobutylureido]-3-(2-naphthyl)propionic acid (compound No. 5-66)

EXAMPLE 6

(2S)-2-[3-(2-Ethoxycarbonylethyl)-3-isobutylureido]-3-(2-naphthyl)propionic acid (compound No. 6-1)

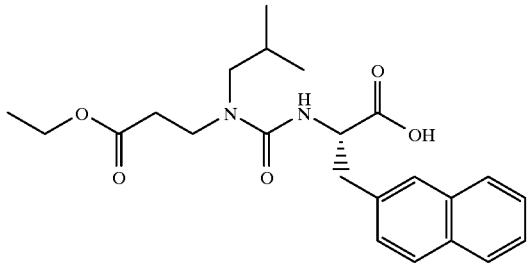

To a solution of benzyl(2S)-2-[3-(2-ethoxycarbonylethyl)-3-isobutylureido]-3-(2-naphthyl)propionate (compound No. 1-23, 687 mg) in ethanol (14 ml) is added 20% palladium hydroxide on carbon (70 mg) under a nitrogen atmosphere. The mixture is stirred under a hydrogen atmosphere for 4.5 hours. The palladium hydroxide on carbon is removed by Celite filtration, and the filtrate is concentrated in vacuo. The oily residue is purified by silica gel column chromatography to give 401 mg (71.1%) of the titled compound (compound No. 6-1).

mp 92.0–95.2° C. (hexane-ethyl acetate)

$[\alpha]_D^{20}$ –34.6° (c=0.99, chloroform)

IR (KBr, cm$^{-1}$) 3413, 2962, 1737, 1715, 1603, 1532, 1454, 1318, 1187, 748.

The following compounds can be prepared by a method similar to Example 6.

(2S)-2-[3-(2-Carboxyethyl)-3-isobutylureido]-3-[2-(6-methoxy)naphthyl]propionic acid (compound No. 6-2)
mp 100–127° C.
$[\alpha]_D^{20}$ –7.9° (c=0.99, dimethyl sulfoxide)
IR (KBr, cm$^{-1}$) 3351, 2960, 2600, 1727, 1636, 1608, 1265, 1230, 1031, 852, 809.

(2S)-2-[3-[(2RS)-2-Carboxy-4-phenylbutyl]-3-isobutylureido]-3-[2-(6-methoxy)naphthyl]propionic acid (compound No. 6-3)

(2S)-2-[3-(2-Methoxycarbonylethyl)-3-isobutylureido]-3-(4-biphenylyl)propionic acid (compound No. 6-4)
mp 82.5–85.0° C.

$[\alpha]_D^{20}$ –36.5° (c=1.0, chloroform)
IR (KBr, cm$^{-1}$) 3353, 2956, 1733, 1611, 1522, 1470, 1378, 1278, 1206.

(2S)-2-[3-(2-Butoxycarbonylethyl)-3-isobutylureido]-3-(4-biphenylyl)propionic acid (compound No. 6-5)
mp 76.7–78.3° C. (diisopropyl ether)
$[\alpha]_D^{20}$ –41.5° (c=0.97, chloroform)
IR (KBr, cm$^{-1}$) 3372, 2956, 1739, 1719, 1606, 1524, 1190, 762, 694.

(2S)-2-[3-(2-Isopropoxycarbonylethyl)-3-isobutylureido]-3-(4-biphenylyl)propionic acid (compound No. 6-6)
mp 114.5–115.5° C. (diethyl ether-hexane)
$[\alpha]_D^{20}$ –11.9° (c=1.0, methanol)
IR (KBr, cm$^{-1}$) 3401, 2966, 1731, 1714, 1634, 1521, 1195, 763.

(2S)-2-[3-(2-Isobutoxycarbonylethyl)-3-isobutylureido]-3-(4-biphenylyl)propionic acid (compound No. 6-7)
mp 64.1–66.7° C.
$[\alpha]_D^{20}$ –39.5° (c=1.0, chloroform)
IR (KBr, cm$^{-1}$) 3379, 2961, 1765, 1738, 1720, 1611, 1530, 1490, 1467, 1382, 1280, 1195.

(2S)-2-[3-[2-(4-Acetamido)phenoxycarbonylethyl]-3-isobutylureido]-3-(4-biphenylyl)propionic acid (compound No. 6-8)
mp 100–107° C. (decomp.)
$[\alpha]_D^{20}$ –4.9° (c=0.99, chloroform)
IR (KBr, cm$^{-1}$) 3307, 2960, 1753, 1671, 1629, 1538, 1507, 1488, 1193, 697.

(2S)-2-[3-(2-Butoxycarbonylethyl)-3-isobutylureido]-3-(2-naphthyl)propionic acid (compound No. 6-9)
mp 106.2–108.5° C. (diisopropyl ether)
$[\alpha]_D^{20}$ –34.8° (c=1.0, chloroform)
IR (KBr, cm$^{-1}$) 3494, 3052, 2958, 1730, 1705, 1605, 1536, 1451, 1414, 1193, 816, 749, 665.

(2S)-2-[3-[(2S or 2R)-2-Ethoxycarbonyl-4-phenylbutyl]-3-isobutylureido]-3-(2-naphthyl)propionic acid (compound No. 6-10)
Diastereomer of compound No. 6-11
$[\alpha]_D^{20}$ –21.7° (c=0.95, dimethyl sulfoxide)
IR (film, cm$^{-1}$) 3437, 2960, 1728, 1603, 1524, 1454, 1382, 1198, 752.

(2S)-2-[3-[(2R or 2S)-2-Ethoxycarbonyl-4-phenylbutyl]-3-isobutylureido]-3-(2-naphthyl)propionic acid (compound No. 6-11)
Diastereomer of compound No. 6-10

(2S)-2-[3-[(2S or 2R)-2-Butoxycarbonyl-4-phenylbutyl]-3-isobutylureido]-3-(2-naphthyl)propionic acid (compound No. 6-12)
$[\alpha]_D^{20}$ +2.7° (c=1.0, chloroform)
IR (film, cm$^{-1}$) 3435, 2959, 1728, 1603, 1524, 1454, 1369, 1198, 753.

EXAMPLE 7

(2S)-2-[3-(2-Carboxyethyl)-3-isobutylureido]-3-[4-(2-nitro)biphenylyl]propionic acid (compound No. 7-1)

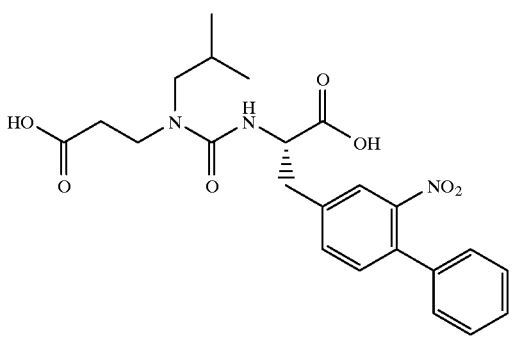

To a solution of benzyl(2S)-2-[3-(2-benzyloxycarbonylethyl)-3-isobutylureido]-3-[4-(2-nitro) biphenylyl]propionate (compound No. 1-17, 457 mg) in ethanol (14.4 ml) is added 1 N lithium hydroxide (1.44 ml). The mixture is stirred for two hours. To the reaction mixture is added 1 N hydrochloric acid to neutralize the mixture. The resulting mixture is concentrated in vacuo to remove ethanol. To the obtained solution is added a 10% aqueous citric acid solution, and the whole is extracted with chloroform. The organic layer is washed with a saturated sodium chloride solution, dried over anhydrous magnesium sulfate, and concentrated in vacuo. The oily residue is purified by silica gel column chromatography to give 230 mg (69.9%) of the titled compound (compound No. 7-1) as amorphous powder.

$[\alpha]_D^{20}$ −20.1° (c=1.0, methanol)

IR (KBr, cm$^{-1}$) 2961, 1723, 1606, 1530, 1362, 1201, 758, 701.

The following compounds can be prepared by a method similar to Example 7.

(2S)-2-[3-(2-Carboxyethyl)-3-isobutylureido]-3-(1,1':4',1"-terphenyl-4-yl)propionic acid (compound No. 7-2)
mp 147.8–150.2° C. (decomp.)
$[\alpha]_D^{20}$ −6.6° (c=0.32, methanol)
IR (KBr, cm$^{-1}$) 2963, 1724, 1614, 1523, 1467, 1217.

(2S)-3-(4-Biphenylyl)-2-[3-[(2RS)-2-carboxy-5-methylhexyl]-3-isobutylureido]propionic acid (compound No. 7-3)
$[\alpha]_D^{20}$ −46.0° (c=0.97, chloroform)
IR (KBr, cm$^{-1}$) 3438, 2958, 1731, 1610, 1527, 1487, 1198, 757, 697.

(2S)-3-(4-Biphenylyl)-2-[3-[(2RS)-2-carboxy-3-phenylpropyl]-3-isobutylureido]propionic acid (compound No. 7-4)
$[\alpha]_D^{20}$ −32.3° (c=1.0, chloroform)
IR (KBr, cm$^{-1}$) 3500–3000 (broad), 2960, 1727, 1602, 1524, 1487,1447, 1201.

(2S)-2-[3-(2-Carboxyethyl)-3-isobutylureido]-3-[4-(4'-chloro)biphenylyl]propionic acid (compound No. 7-5)
$[\alpha]_D^{20}$ −36.1° (c=0.34, dimethyl sulfoxide)
IR (KBr, cm$^{-1}$) 2961, 1717, 1609, 1532, 1486, 1213, 1141, 1094

(2S)-2-[3-[(2RS)-2-Carboxy-4-phenylbutyl]-3-isobutylureido]-3-(2-naphthyl)propionic acid (compound No. 7-6)
$[\alpha]_D^{20}$ −41.4° (c=1.0, chloroform)
IR (KBr, cm$^{-1}$) 3438, 2959, 1733, 1602, 1525, 1454, 1200, 745, 700.

(2S)-3-[2-(1-Bromo)naphthyl]-2-[3-(2-carboxyethyl)-3-isobutylureido]propionic acid (compound No. 7-7)
IR (KBr, cm$^{-1}$) 3641, 2958, 1724, 1609, 1526, 1431, 1152, 862, 814, 768.

(2S)-2-[3-[(2RS)-2-(2-Acetamidoethoxycarbonyl)-2-benzyloxyethyl]-3-isobutylureido]-3-(4-biphenylyl) propionic acid (compound No. 7-8)

(2S)-2-[3-[(2RS)-2-Benzyloxy-2-(2-methoxyphenoxycarbonyl)ethyl]-3-isobutylureido]-3-(4-biphenylyl)propionic acid (compound No. 7-9)

(2S)-2-[3-[(2RS)-2-Benzyloxy-2-(5-indanyloxycarbonyl) ethyl]-3-isobutylureido]-3-(4-biphenylyl)propionic acid (compound No.7-10)

(2S)-2-[3-(2-Carboxyethyl)-3-isobutylureido]-3-[4-(4'-methyl-2-nitro)biphenylyl]propionic acid (compound No. 7-11)

(2S)-2-[3-(2-Carboxyethyl)-3-isobutylureido]-3-[4-(3'-nitro)biphenylyl]propionic acid (compound No.7-12)

(2S)-2-[3-[(2RS)-2-Carboxy-4-phenylbutyl]-3-isobutylureido]-3-[4-(4'-chloro)biphenylyl]propionic acid (compound No. 7-13)

(2S)-2-[3-[(2RS)-2-Carboxy-4-phenylbutyl]-3-isobutylureido]-3-[4-(4'-methyl-2-nitro)biphenylyl] propionic acid (compound No.7-14)

(2S)-2-[3-[(2RS)-2-Carboxy-4-phenylbutyl]-3-isobutylureido]-3-[4-(3'-nitro)biphenylyl]propionic acid (compound No. 7-15)

(2S)-2-[3-[(2RS)-2-Carboxy-4-phenylbutyl]-3-isobutylureido]-3-[4 -(2-nitro)biphenylyl]propionic acid (compound No. 7-16)

(2S)-2-[3-[(2RS)-2-Carboxy-4-phenylbutyl]-3-isobutylureido]-3-(1,1':4',1"-terphenyl-4-yl)propionic acid (compound No. 7-17)

(2S)-3-[2-(1-Bromo)naphthyl]-2-[3-[(2RS)-2-carboxy-4-phenylbutyl]-3-isobutylureido]propionic acid (compound No. 7-18)

(2S)-2-[3-Benzyl-3-[(2RS)-2-carboxy-4-phenylbutyl] ureido]-3-(4-biphenylyl)propionic acid (compound No. 7-19)

(2S)-2-[3-Benzyl-3-[(2RS)-2-carboxy-4-phenylbutyl] ureido]-3-(2-naphthyl)propionic acid (compound No. 7-20)

(2S)-2-[3-[(2RS)-2-Benzyloxy-2-carbamoylethyl]-3-isobutylureido]-3-(4-biphenylyl)propionic acid (compound No. 7-21)

EXAMPLE 8

(2S)-2-[3-[(2S or 2R)-2-Benzyloxy-2-carboxyethyl]-3-isobutylureido]-3-(4-biphenylyl)propionic acid (compound No. 8-1) and (2S)-2-[3-[(2R or 2S)-2-benzyloxy-2-carboxyethyl]-3-isobutylureido]-3-(4-biphenylyl)propionic acid (compound No. 8-2)

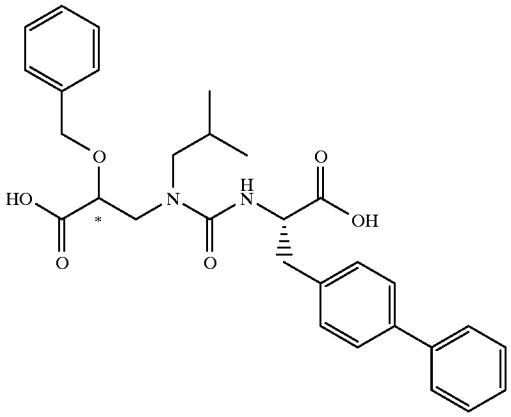

To a solution of benzyl(2S)-2-[3-[(2RS)-2-benzyloxy-2-benzyloxycarbonylethyl]-3-isobutylureido]-3-(4-biphenylyl)propionate (compound No. 1-11, 252 mg) in methanol (1.6 ml)-chloroform (1 ml) is added 1 N lithium hydroxide (0.8 ml). The mixture is stirred for three hours. To the reaction mixture is added a 10% aqueous citric acid solution to neutralize the mixture. The resulting mixture is concentrated in vacuo to remove methanol and chloroform. To the obtained solution is added a 10% aqueous citric acid solution, and the whole is extracted with ethyl acetate. The organic layer is washed with a saturated sodium chloride solution, dried over anhydrous sodium sulfate, and concentrated in vacuo. The oily residue is purified by silica gel column chromatography to give 69 mg (37%) and 64 mg (34%) of the titled compounds (compound Nos. 8-1 and 8-2) as amorphous powder respectively.

(2S)-2-[3-[(2S or 2R)-2-Benzyloxy-2-carboxyethyl]-3-isobutylureido]-3-(4-biphenylyl)propionic acid (compound No. 8-1)
Diastereomer of compound No. 8-2
$[\alpha]_D^{20}$ −44.6° (c=0.36, chloroform)
IR (KBr, cm$^{-1}$) 2960, 1740, 1607, 1530, 1210, 1114, 759, 698.

(2S)-2-[3-[(2R or 2S)-2-Benzyloxy-2-carboxyethyl]-3-isobutylureido]-3-(4-biphenylyl)propionic acid (compound No. 8-2)
Diastereomer of compound No. 8-1
$[\alpha]_D^{20}$ −69.8° (c=0.36, chloroform)
IR (KBr, cm$^{-1}$) 3321, 2960, 1732, 1611, 1530, 1209, 1112, 758, 698.

The following compounds can be prepared by a method similar to Example 8.

(2S)-2-[3-[(2S or 2R)-2-Benzyloxy-2-carboxyethyl]-3-isobutylureido]-3-(2-naphthyl)propionic acid (compound No. 8-3)
Diastereomer of compound No. 8-4
$[\alpha]_D^{20}$ −39.0° (c=1.0, chloroform)
IR (KBr, cm$^{-1}$) 3500–3000 (broad), 2957, 1719, 1603, 1529, 1454, 1209, 1109.

(2S)-2-[3-[(2R or 2S)-2-Benzyloxy-2-carboxyethyl]-3-isobutylureido]-3-(2-naphthyl)propionic acid (compound No. 8-4)
Diastereomer of compound No. 8-3
$[\alpha]_D^{20}$ −56.0° (c=1.0, chloroform)
IR (KBr, cm$^{-1}$) 3500–3000 (broad), 2958, 1736, 1601, 1528, 1454, 1213, 1113.

EXAMPLE 9

(2S)-3-(4-Biphenylyl)-2-[3-[(2S or 2R)-2-carboxy-4-phenylbutyl]-3-isobutylureido]propionic acid (compound No. 9-1)

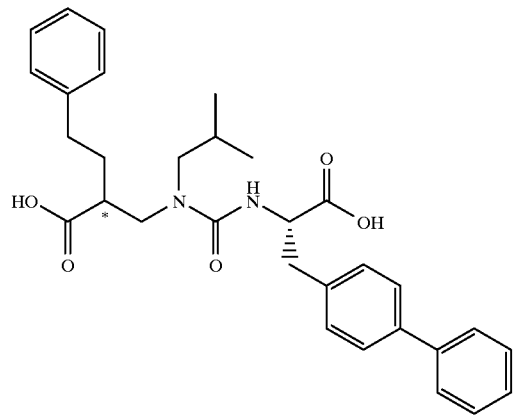

To benzyl(2S)-3-(4-biphenylyl)-2-[3-[(2S or 2R)-2-tert.butoxycarbonyl-4-phenylbutyl]-3-isobutylureido] propionate (compound No. 1-84, 190 mg) is added 4.0 N hydrochloric acid/dioxane (1.45 ml). The mixture is stirred at room temperature for 9.5 hours. The reaction mixture is concentrated in vacuo. The oily residue is dissolved in methanol (4 ml). To the solution is added 20% palladium hydroxide on carbon (40 mg) under a nitrogen atmosphere. The mixture is stirred under a hydrogen atmosphere for 45 minutes. Palladium on carbon is removed by Celite filtration, and the filtrate is concentrated in vacuo. The oily residue is purified by silica gel column chromatography to give 87.4 mg (61.5%) of the titled compound (compound No. 9-1) as amorphous powder.

Single diastereomer of compound No.5-6
Diastereomer of compound No. 9-2
$[\alpha]_D^{20}$ −23.3° (c=0.28, chloroform)
IR (KBr, cm$^{-1}$) 3435, 2958, 1728, 1606, 1524, 1454, 1204, 757, 698.

The following compounds can be prepared by a method similar to Example 9.

(2S)-3-(4-Biphenylyl)-2-[3-[(2R or 2S)-2-carboxy-4-phenylbutyl]-3-isobutylureido]propionic acid (compound No. 9-2)
Single diastereomer of compound No. 5-6
Diastereomer of compound No. 9-1
$[\alpha]_D^{20}$ −62.2° (c=0.32, chloroform)
IR (KBr, cm$^{-1}$) 2958, 1728, 1603, 1523, 1453, 1204, 757, 698.

(2S)-2-[3-[(2S or 2R)-2-Carboxy-4-phenylbutyl]-3-isobutylureido]-3-(2-naphthyl)propionic acid (compound No. 9-3)
Single diastereomer of compound No. 7-6
Diastereomer of compound No. 9-4
$[\alpha]_D^{20}$ −27.2° (c=0.50, chloroform)
IR (KBr, cm$^{-1}$) 3435, 2957, 1730, 1602, 1525, 1454, 1201, 746, 700.

(2S)-2-[3-[(2R or 2S)-2-Carboxy-4-phenylbutyl]-3-isobutylureido]-3-(2-naphthyl)propionic acid (compound No. 9-4)

Single diasteromer of compound No. 7-6
Diastereomer of compound No. 9-3
[α]$_D^{20}$ −55.2° (c=0.49, chloroform)
IR (KBr, cm$^{-1}$) 2959, 1730, 1603, 1526, 1454, 1204, 745, 699.

EXAMPLE 10

(2S)-3-(4-Biphenylyl)-2-[3-[(2S or 2R)-2-hydroxycarbamoyl-4-phenylbutyl]-3-isobutylureido] propionic acid (compound No. 10-1)

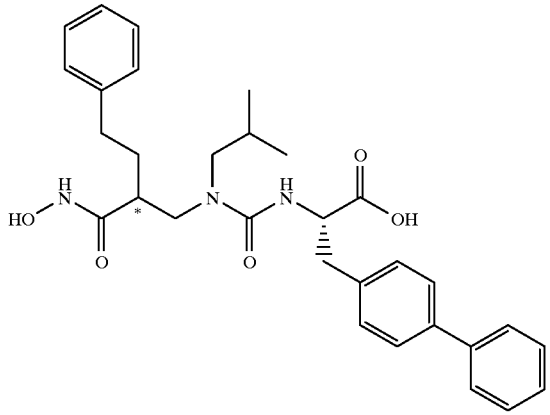

1) Benzyl(2S)-3-(4-biphenylyl)-2-[3-[(2S or 2R)-2-carboxy-4-phenylbutyl]-3-isobutylureido]propionate (compound No. 3-19, 125 mg), o-benzylhydroxyamine hydrochloride (66 mg) and 1-hydroxybenzotriazole (28 mg) are suspended in methylene chloride (2.5 ml). To the suspension are added N-methylmorpholine (0.09 ml) and 1-ethyl-3-(3-dimethylaminopropyl)carbodiimide hydrochloride (40 mg) under a nitrogen atmosphere. The mixture is stirred at room temperature for two hours. The reaction mixture is concentrated in vacuo. Water is added to the oily residue, and the whole is extracted with ethyl acetate. The organic layer is sequentially washed with 10% citric acid, a saturated sodium bicarbonate solution and a saturated sodium chloride solution, dried over anhydrous sodium sulfate, and concentrated in vacuo. The oily residue is purified by silica gel column chromatography to give 130 mg (89%) of benzyl(2S)-3-(4-biphenylyl)-2-[3-[(2S or 2R)-2-benzyloxycarbamoyl-4-phenylbutyl]-3-isobutylureido] propionate.

[α]$_D^{20}$ −40.4° (c=0.36, methanol)
IR (film, cm$^{-1}$) 3445, 3184, 3028, 2958, 1953, 1879, 1741, 1632, 1518, 1454, 1386, 1175, 1027, 753, 696.

2) To a solution of benzyl(2S)-3-(4-biphenylyl)-2-[3-[(2S or 2R)-2-benzyloxycarbamoyl-4-phenylbutyl]-3-isobutylureido]propionate (109 mg) in tetrahydrofuran (5 ml) is added 20% palladium hydroxide on carbon (12 mg) under a nitrogen atmosphere. The mixture is stirred under a hydrogen atmosphere for four hours. The palladium hydroxide on carbon is removed by Celite purified on, and the filtrate is concentrated in vacuo. The oily residue is purified by silica gel column chromatography to give 51 mg (63%) of the titled compound (compound No. 10-1) as amorphous powder.

Single diasteromer of compound No. 3-14
Diastereomer of compound No. 10-2
[α]$_D^{20}$ −15.5° (c=0.12, chloroform)
IR (KBr, cm$^{-1}$) 3202, 3029, 2925, 1880, 1725, 1626, 1519, 1453, 1204, 1030, 1009, 756, 698.

The following compounds can be prepared by a method similar to Example 10.
(2S)-3-(4-Biphenylyl)-2-[3-[(2R or 2S)-2-hydroxycarbamoyl-4-phenylbutyl]-3-isobutylureido] propionic acid (compound No. 10-2)
Single diasteromer of compound No. 3-14
Diastereomer of compound No. 10-1
(2S)-3-(4-Biphenylyl)-2-[3-[(2S or 2R)-2-hydroxycarbamoyl-5-methylhexyl]-3-isobutylureido] propionic acid (compound No. 10-3)
Single diasteromer of compound No. 3-12
Diastereomer of compound No. 10-4
(2S)-3-(4-Biphenylyl)-2-[3-[(2R or 2S)-2-hydroxycarbamoyl-5-methylhexyl]-3-isobutylureido] propionic acid (compound No. 10-4)
Single diasteromer of compound No. 3-12
Diastereomer of compound No. 10-3
(2S)-3-(4-Biphenylyl)-2-[3-[(2S or 2R)-2-hydroxycarbamoyl-3-phenylpropyl]-3-isobutylureido] propionic acid (compound No. 10-5)
Single diasteromer of compound No. 3-13
Diastereomer of compound No. 10-6
(2S)-3-(4-Biphenylyl)-2-[3-[(2R or 2S)-2-hydroxycarbamoyl-3-phenylpropyl]-3-isobutylureido] propionic acid (compound No. 10-6)
Single diasteromer of compound No. 3-13
Diastereomer of compound No. 10-5
(2S)-2-[3-[(2S or 2R)-2-Benzyloxy-2-hydroxycarbamoylethyl]-3-isobutylureido]-3-(4-biphenylyl)propionic acid (compound No. 10-7)
Single diasteromer of compound No. 3-16
Diastereomer of compound No. 10-8
(2S)-2-[3-[(2R or 2S)-2-Benzyloxy-2-hydroxycarbamoylethyl]-3-isobutylureido]-3-(4-biphenylyl)propionic acid (compound No. 10-8)
Single diasteromer of compound No. 3-16
Diastereomer of compound No. 10-7
(2S)-2-[3-[(2S or 2R)-2-Hydroxycarbamoyl-4-phenylbutyl]-3-isobutylureido]-3-(2-naphthyl)propionic acid (compound No. 10-9)
Single diasteromer of compound No. 3-17
Diastereomer of compound No. 10-10
(2S)-2-[3-[(2R or 2S)-2-Hydroxycarbamoyl-4-phenylbutyl]-3-isobutylureido]-3-(2-naphthyl)propionic acid (compound No. 10-10)
Single diasteromer of compound No. 3-17
Diastereomer of compound No. 10-9
(2S)-3-(4-Biphenylyl)-2-[3-(2-hydroxycarbamoylethyl)-3-isobutylureido]propionic acid (compound No. 3-10) can also be synthesized by a method similar to Example 10.

Formulation

General formulation examples of oral preparations and injections using the present compounds are shown below.

1) Tablet

Prescription 1 in 100 mg

| | |
|---|---|
| present compound | 1 mg |
| lactose | 66.4 mg |
| cornstarch | 20 mg |
| calcium carboxymethylcellulose | 6 mg |
| hydroxypropylcellulose | 4 mg |
| magnesium stearate | 0.6 mg |

Tablets according to the prescription as above were coated with 2 mg/tablet of a coating agent (this is an ordinary coating agent such as hydroxypropylmethylcellulose, macrogol or silicone resin) to obtain desired coated tablets. (The same is applied to tablets mentioned below.)

Prescription 2 in 100 mg

| present compound | 5 mg |
|---|---|
| lactose | 62.4 mg |
| cornstarch | 20 mg |
| calcium carboxymethylcellulose | 6 mg |
| hydroxypropylcellulose | 4 mg |
| magnesium stearate | 0.6 mg |
| coating agent | 2 mg |

Prescription 3 in 100 mg

| present compound | 20 mg |
|---|---|
| lactose | 51 mg |
| cornstarch | 15 mg |
| calcium carboxymethylcellulose | 5 mg |
| hydroxypropylcellulose | 5 mg |
| magnesium stearate | 1 mg |
| talc | 1 mg |
| coating agent | 2 mg |

Prescription 4 in 100 mg

| present compound | 40 mg |
|---|---|
| lactose | 34 mg |
| cornstarch | 10 mg |
| calcium carboxymethylcellulose | 5 mg |
| hydroxypropylcellulose | 5 mg |
| magnesium stearate | 2 mg |
| talc | 2 mg |
| coating agent | 2 mg |

Prescription 5 in 220 mg

| present compound | 100 mg |
|---|---|
| lactose | 67 mg |
| cornstarch | 20 mg |
| calcium carboxymethylcellulose | 10 mg |
| hydroxypropylcellulose | 10 mg |
| magnesium stearate | 4 mg |
| talc | 4 mg |
| coating agent | 5 mg |

2) Capsule

Prescription 1 in 150 mg

| present compound | 5 mg |
|---|---|
| lactose | 145 mg |

Varying the mixing ratio of the present compound to lactose, capsules having the contents of the present compound of 10 mg/capsule, 30 mg/capsule, 50 mg/capsule and 100 mg/capsule were also prepared.

3) Granule

Prescription 1 in 100 mg

| present compound | 30 mg |
|---|---|
| mannitol | 46.5 mg |
| polyvinyl pyrrolidone K-30 | 7 mg |
| eudragit RL | 15 mg |
| triacetin | 1.5 mg |

Prescription 2 in 130 mg

| present compound | 50 mg |
|---|---|
| lactose | 55 mg |
| white potato starch | 20 mg |
| hydroxypropylcellulose | 4 mg |
| talc | trace |

4) Injection

Prescription 1 in 10 ml

| present compound | 10–100 mg |
|---|---|
| sodium chloride | 90 mg |
| sodium hydroxide | q.s. |
| sterile purified water | q.s. |

EFFECT OF THE INVENTION

Pharmacological Test

As a method for measuring endopeptidase 24.11 activity, Florentin et al. had reported a method for measuring the enzyme activity by a degree of cleavage of a peptide bond between glycine and p-nitrophenylalanine using N-dansyl-D-alanyl-glycyl-p-nitrophenylalanyl-glycine (DAGNPG) as a substrate (Anal. Biochem., 141, 62–69 (1984)). An effect of the present compounds on endopeptidase 24.11 was examined according to the method described in the literature.

Experimental Method

An enzyme preparation used in this pharmacological test was prepared by extracting from a rat kidney by the following method according to the method of Malfloy et al. (J. Biol. Chem., 259, 14365–14370 (1984)).

A kidney was excised from a Wistar rat. The kidney was homogenized in Tris-hydrochloric acid buffer (5 mM, pH 7.4, containing 125 mM D-mannitol and 12 mM magnesium chloride). The homogenate was centrifuged at low speed (1,000×g) to give a supernatant. The supernatant was ultracentrifuged (7,000×g) for 120 minutes. The resulting pellet was suspended in Tris-hydrochloric acid buffer (2.5 mM, pH 7.4, containing 62.5 mM D-mannitol and 6 mM magnesium chloride). The suspension was centrifuged at low speed and then ultracentrifuged again. The resulting pellet was suspended in HEPES buffer (5 mM, pH 7.4) to give the enzyme preparation.

In order to examine the effect of the present compounds on the enzyme preparation, reactions were performed under the following condition using mixed solutions consisting of the composition shown in Table 1.

TABLE 1

| Tris-hydrochloric acid buffer (pH 7.4) | 50 mM |
|---|---|
| DAGNPG | 50 µM |
| Enzyme preparation | 0.3–0.5 µg protein |
| Test compounds | $10^{-11} - 10^{-4}$ M |

The above-mentioned solution (150 µl) was incubated at 37° C. for 30 minutes and then boiled at 100° C. for five minutes. To the solution was added 1.35 ml of Tris-hydrochloric acid buffer (50 mM, pH 7.4). The mixture was centrifuged at moderate speed (5,000×g) for five minutes to give a supernatant. Fluorescence intensity of the supernatant (excitation at 342 nm of wave length and emission at 562 nm) was measured.

45

The degree of the inhibitory effect of each test compound on the enzyme preparation is expressed by the inhibition rate calculated by the following equation.

$$\text{Inhibition rate (\%)} = \frac{A - B}{A} \times 100$$

A: fluorescence intensity of the sample in the absence of the test compound

B: fluorescence intensity of the sample in the presence of the test compound

Result

As examples of the experimental results, Table 2 shows concentrations of compound Nos. 5-1, 5-6, 5-21, 7-3, 7-6, 8-1, 9-1 and 10-1 required to inhibit endopeptidase 24.11 by 50%, i.e., $IC_{50}$.

TABLE 2

| | $IC_{50}$ (M) |
|---|---|
| Compound No. 5-1 | $1.3 \times 10^{-9}$ |
| Compound No. 5-6 | $5.5 \times 10^{-10}$ |
| Compound No. 5-21 | $9.3 \times 10^{-9}$ |
| Compound No. 7-3 | $4.0 \times 10^{-9}$ |
| Compound No. 7-6 | $3.1 \times 10^{-9}$ |
| Compound No. 8-1 | $9.3 \times 10^{-10}$ |
| Compound No. 9-1 | $5.8 \times 10^{-10}$ |
| Compound No. 10-1 | $2.1 \times 10^{-9}$ |

As shown in Table 2, the present compounds were found to inhibit the endopeptidase 24.11 activity remarkably at the low concentrations.

Since the above-mentioned results show that the present compounds have the excellent inhibitory effects on endopeptidase 24.11, it is apparent that the compounds have wide medical uses as therapeutic agents for diseases in which endopeptidase 24.11 is concerned, for example, cardiovascular diseases such as heart failure and hypertension, renal diseases such as renal failure, gastroenteric disorders such as diarrhea and hyperchlorhydria, endocrine and metabolic diseases such as obesity, and autoimmune diseases such as rheumatic disease, and as analgestics for myosalgia, migraine, etc. Coupled with the fact that the compounds also have an inhibitory activity on angiotensin-converting enzyme, it is apparent that the compounds are particularly useful as therapeutic agents for cardiovascular diseases such as heart failure and hypertension.

Industrial Applicability

The present invention relates to a novel 1,3-dialkylurea derivative which has inhibitory effects on endopeptidase 24.11 and is useful as therapeutic agents for cardiovascular diseases such as heart failure and hypertension, renal diseases such as renal failure, gastroenteric disorders such as diarrhea and hyperchlorhydria, endocrine and metabolic diseases such as obesity, and autoimmune diseases such as rheumatic disease, and as analgestics for myosalgia, migraine, etc.

We claim:

1. A compound represented by the formula (I) or a salt thereof,

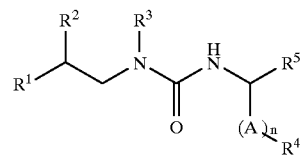

(I)

wherein
$R^1$ represents a carboxyl group or a carboxyl group which is converted into an ester thereof, an amide thereof or a hydroxamic acid thereof, a phosphonic group or a phosphonic group which is converted into an ester;

$R^2$ represents a hydrogen atom, a lower alkyl group, a phenyl lower alkyl group, a lower alkoxy group or a phenyl lower alkoxy group, and each phenyl ring of the phenyl lower alkyl group and the phenyl lower alkoxy group is unsubstituted or substituted by a halogen atom, a lower alkyl group, a hydroxy group, a lower alkoxy group, a lower alkylenedioxy group, a nitro group, an amino group or a lower alkylamino group;

$R^3$ represents a lower alkyl group or a phenyl lower alkyl group, and the phenyl ring of the phenyl lower alkyl group is unsubstituted or substituted by a halogen atom, a lower alkyl group, a hydroxy group, a lower alkoxy group or a lower alkylenedioxy group;

$R^5$ represents a carboxyl group or a carboxyl group which is converted into an ester thereof, an amide thereof or a hydroxamic acid thereof, a phosphonic group or a phosphonic group which is converted into an ester thereof;

$R^4$ represents a group represented by the formula (XI), (XII) or (XIII),

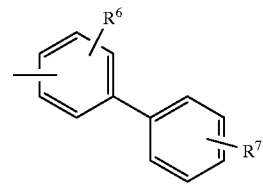

(XI)

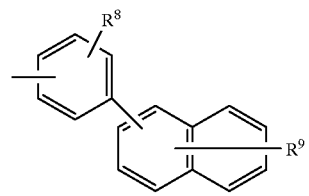

(XII)

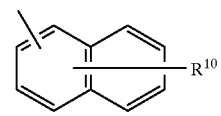

(XIII)

wherein
$R^6$ represents a hydrogen atom, a halogen atom, a lower alkyl group, a hydroxy group, a lower alkoxy group, a lower alkylenedioxy group, a nitro group, an amino group or a lower alkylamino group;

$R^7$ represents a hydrogen atom, a halogen atom, a lower alkyl group, a hydroxy group, a lower alkoxy group, a lower alkylenedioxy group, a nitro group, an amino group, a lower alkylamino group, a phenyl group which is unsubstituted or has a substituent, and said substituent is a halogen atom, a lower alkyl group, a hydroxy group, a lower alkoxy group, a lower alkylenedioxy group, a nitro group, an amino group or a lower alkylamino group;

$R^8$ represents a hydrogen atom, a halogen atom, a lower alkyl group, a hydroxy group, a lower alkoxy group, a lower alkylenedioxy group, a nitro group, an amino group or a lower alkylamino group;

$R^9$ represents a hydrogen atom, a halogen atom, a lower alkyl group, a hydroxy group, a lower alkoxy group, a lower alkylenedioxy group, a nitro group, an amino group, a lower alkylamino group, a phenyl group which is unsubstituted or has a substituent or a naphthyl group which is unsubstituted or has a substituent, and said substituent is a halogen atom, a lower alkyl group, a hydroxy group, a lower alkoxy group, a lower alkylenedioxy group, a nitro group, an amino group or a lower alkylamino group;

$R^{10}$ represents a hydrogen atom, a halogen atom, a lower alkyl group, a hydroxy group, a lower alkoxy group, a lower alkylenedioxy group, a nitro group, an amino group, a lower alkylamino group, a phenyl group which is unsubstituted or has a substituent or a naphthyl group which is unsubstituted or has a substituent, and said substituent is a halogen atom, a lower alkyl group, a hydroxy group, a lower alkoxy group, a lower alkylenedioxy group, a nitro group, an amino group or a lower alkylamino group;

A represents a lower alkylene group; and n represents 0 or 1.

2. A compound represented by the formula (I) or a salt thereof,

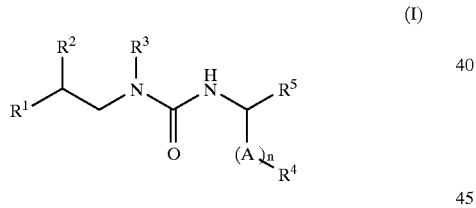
(I)

wherein $R^1$ represents a carboxyl group or a carboxyl group which is converted into a lower alkyl ester thereof, a lower alkanoylamino-lower alkyl ester thereof, a phenyl lower alkyl ester thereof, a phenyl ester thereof or an indanyl ester thereof; a carboxyl group which is converted into an amide thereof with ammonia, a lower alkylamine or a phenyl lower alkylamine; a carboxyl group which is converted into a hydroxamic acid thereof; a phosphonic group or a phosphonic group which is converted into a lower alkyl ester thereof, and each phenyl ring of the phenyl lower alkyl ester, the phenyl ester and the phenyl lower alkylamine is unsubstituted or substituted by a halogen atom, a lower alkyl group, a hydroxy group, a lower alkoxy group, a lower alkylenedioxy group, a nitro group, an amino group, a lower alkyl amino group or a lower alkanoylamino group;

$R^2$ represents a hydrogen atom, a lower alkyl group, a phenyl lower alkyl group, a lower alkoxy group or a phenyl lower alkoxy group, and each phenyl ring of the phenyl lower alkyl group and the phenyl lower alkoxy group is unsubstituted or substituted by a halogen atom, a lower alkyl group, a hydroxy group, a lower alkoxy group, a lower alkylenedioxy group, a nitro group, an amino group or a lower alkylamino group;

$R^3$ represents a lower alkyl group or a phenyl lower alkyl group, and the phenyl ring of the phenyl lower alkyl group is unsubstituted or substituted by a halogen atom, a lower alkyl group, a hydroxy group, a lower alkoxy group or a lower alkylenedioxy group;

$R^5$ represents a carboxyl group or a carboxyl group which is converted into a lower alkyl ester thereof, a lower alkanoylamino-lower alkyl ester thereof, a phenyl lower alkyl ester thereof, a phenyl ester thereof or an indanyl ester thereof; a carboxyl group which is converted into an amide thereof with ammonia, a lower alkylamine or a phenyl lower alkylamine; a carboxyl group which is converted into a hydroxamic acid thereof; a phosphonic group or a phosphonic group which is converted into a lower alkyl ester thereof, and each phenyl ring of the phenyl lower alkyl ester, the phenyl ester and the phenyl lower alkylamine is unsubstituted or substituted by a halogen atom, a lower alkyl group, a hydroxy group, a lower alkoxy group, a lower alkylenedioxy group, a nitro group, an amino group, a lower alkylamino group or a lower alkanoylamino group;

$R^4$ represents a group represented by the formula (XI), (XII) or (XIII),

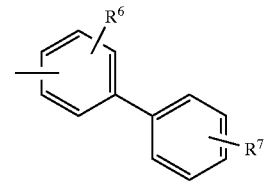
(XI)

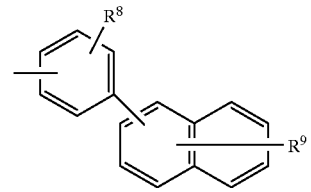
(XII)

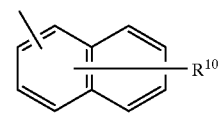
(XIII)

wherein $R^6$ represents a hydrogen atom, a halogen atom, a lower alkyl group, a hydroxy group, a lower alkoxy group, a lower alkylenedioxy group, a nitro group, an amino group or a lower alkylamino group;

$R^7$ represents a hydrogen atom, a halogen atom, a lower alkyl group, a hydroxy group, a lower alkoxy group, a lower alkylamino group, a phenyl group which is unsubstituted or has a substituent or a naphthyl group which is unsubstituted or has a substituent, and said substituent is a halogen atom, a lower alkyl group, a hydroxy group, a lower alkoxy group, a lower alkylenedioxy group, a nitro group, an amino group or a lower alkylamino group;

R⁸ represents a hydrogen atom, a halogen atom, a lower alkyl group, a hydroxy group, a lower alkoxy group, a lower alkylenedioxy group, a nitro group, an amino group or a lower alkylamino group;

R⁹ represents a hydrogen atom, a halogen atom, a lower alkyl group, a hydroxy group, a lower alkoxy group, a lower alkylenedioxy group, a nitro group, an amino group, a lower alkylamino group, a phenyl group which is unsubstituted or has a substituent or a naphthyl group which is unsubstituted or has a substituent, and said substituent is a halogen atom, a lower alkyl group, a hydroxy group, a lower alkoxy group, a lower alkylenedioxy group, a nitro group, an amino group or a lower alkylamino group;

R¹⁰ represents a hydrogen atom, a halogen atom, a lower alkyl group, a hydroxy group, a lower alkoxy group, a lower alkylenedioxy group, a nitro group, an amino group, a lower alkylamino group, a phenyl group which is unsubstituted or has a substituent or a naphthyl group which is unsubstituted or has a substituent, and said substituent is a halogen atom, a lower alkyl group, a hydroxy group, a lower alkoxy group, a lower alkylenedioxy group, a nitro group, an amino group or a lower alkylamino group;

A represents a lower alkylene group; and n represents 0 or 1.

3. A compound represented by the formula (I) or a salt thereof,

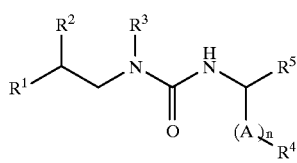

(I)

wherein

R¹ represents a carboxyl group or a carboxyl group which is converted into a lower alkyl ester thereof, a lower alkanoylamino-lower alkyl ester thereof, a phenyl lower alkyl ester thereof, a lower alkoxyphenyl ester thereof, a lower alkanoylaminophenyl ester thereof or an indanyl ester thereof; a carboxyl group which is converted into an amide thereof with ammonia; a carboxyl group which is converted into a hydroxamic acid thereof; a phosphonic group or a phosphonic group which is converted into a lower alkyl ester thereof;

R² represents a hydrogen atom, a lower alkyl group, a phenyl lower alkyl group, a lower alkoxy group or a phenyl lower alkoxy group;

R³ represents a lower alkyl group or a phenyl lower alkyl group;

R⁵ represents a carboxyl group or a carboxyl group which is converted into a lower alkyl ester thereof, a lower alkanoylamino-lower alkyl ester thereof, a phenyl lower alkyl ester thereof, a lower alkoxyphenyl ester thereof, a lower alkanoylaminophenyl ester thereof or an indanyl ester thereof; a carboxyl group which is converted into an amide thereof with ammonia; or a carboxyl group which is converted into a hydroxamic acid thereof;

R⁴ represents a group represented by the formula (XI), (XII) or (XIII),

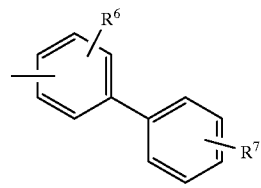

(XI)

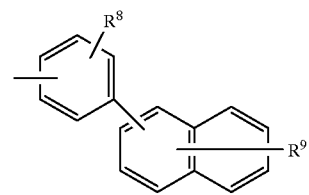

(XII)

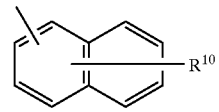

(XIII)

wherein

R⁶ represents a hydrogen atom or a nitro group;

R⁷ represents a hydrogen atom, a halogen atom, a lower alkyl group, a hydroxy group, a lower alkoxy group, a nitro group, an amino group or a phenyl group;

R⁸ and R⁹ each represents a hydrogen atom;

R¹⁰ represents a hydrogen atom, a halogen atom or a lower alkoxy group;

A represents a lower alkylene group; and n represents 1.

4. A compound represented by the formula (I) or a salt thereof,

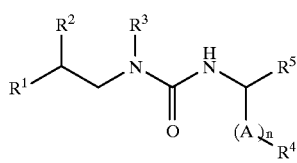

(I)

wherein

R¹ represents a carboxyl group or a carboxyl group which is converted into a lower alkyl ester thereof, a lower alkanoylamino-lower alkyl ester thereof, a phenyl lower alkyl ester thereof, a lower alkoxyphenyl ester thereof, a lower alkanoylaminophenyl ester thereof or an indanyl ester thereof; a carboxyl group which is converted into a hydroxamic acid thereof; a phosphonic group or a phosphonic group which is converted into a lower alkyl ester thereof;

R² represents a hydrogen atom, a lower alkyl group, a phenyl lower alkyl group or a phenyl lower alkoxy group;

R³ represents a lower alkyl group;

R⁵ represents a carboxyl group or a carboxyl group which is converted into a lower alkyl ester thereof, a phenyl lower alkyl ester thereof or a lower alkanoylaminophenyl ester thereof;

R⁴ represents a group represented by the formula (XI), (XII) or (XIII),

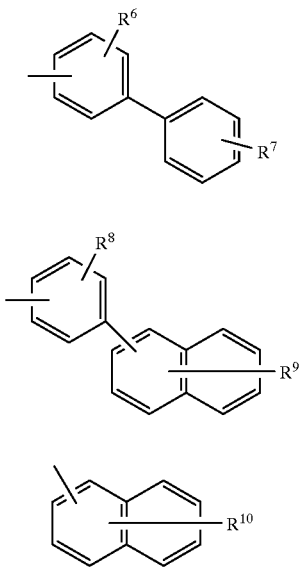

(XI)

(XII)

(XIII)

wherein

R⁶ represents a hydrogen atom or a nitro group;

R⁷ represents a hydrogen atom, a halogen atom, a lower alkyl group, a lower alkoxy group or a phenyl group;

R⁸ and R⁹ each represents a hydrogen atom;

R¹⁰ represents a hydrogen atom, a halogen atom or a lower alkoxy group;

A represents a lower alkylene group; and n represents 1.

5. The compound or a salt thereof as claimed in claim 4, wherein R¹ represents a carboxyl group or a carboxyl group which is converted into an ethyl ester thereof, a butyl ester thereof, an isopropyl ester thereof, an isobutyl ester thereof, a tert.-butyl ester thereof, an acetamidoethyl ester thereof, a benzyl ester thereof, a methoxyphenyl ester thereof, an acetamidophenyl ester thereof or an indanyl ester thereof; a carboxyl group which is converted into a hydroxamic acid thereof; a phosphonic group or a phosphonic group which is converted into an ethyl ester thereof; R² represents a hydrogen atom, an isopentyl group, a benzyl group, a phenethyl group, a phenylpropyl group, a phenylbutyl group or a benzyloxy group; R³ represents an isobutyl group; R⁴ represents a biphenylyl group, a fluorobiphenylyl group, a chlorobiphenylyl group, a methylbiphenylyl group, a methoxybiphenylyl group, a nitrobiphenylyl group, a terphenylyl group, a naphthylphenyl group, a naphthyl group, a bromonaphthyl group or a methoxynaphthyl group; R⁵ represents a carboxyl group or a carboxyl group which is converted into a methyl ester thereof, a benzyl ester thereof or an acetamidophenyl ester thereof; and A represents a methylene group.

6. A compound represented by the formula (I) or a salt thereof,

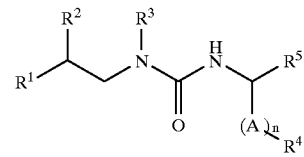

wherein

R¹ represents a carboxyl group or a carboxyl group which is converted into a lower alkyl ester thereof, a phenyl lower alkyl ester thereof, a lower alkoxyphenyl ester thereof or an indanyl ester thereof;

R² represents a hydrogen atom, a lower alkyl group, a phenyl lower alkyl group or a phenyl lower alkoxy group;

R³ represents a lower alkyl group;

R⁵ represents a carboxyl group or a carboxyl group which is converted into a lower alkyl ester thereof or a phenyl lower alkyl ester thereof;

R⁴ represents a group represented by the formula (XI) or (XIII),

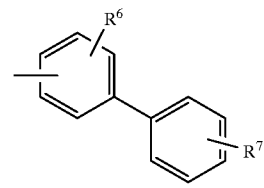

(XI)

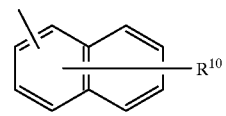

(XIII)

wherein

R⁶ represents a hydrogen atom;

R⁷ represents a hydrogen atom, a halogen atom, a lower alkoxy group or a phenyl group;

R¹⁰ represents a hydrogen atom or a lower alkoxy group;

A represents a lower alkylene group; and n represents 1.

7. The compound or a salt thereof as claimed in claim 6, wherein R¹ represents a carboxyl group or a carboxyl group which is converted into an ethyl ester thereof, a butyl ester thereof, an isopropyl ester thereof, an isobutyl ester thereof, a tert.-butyl ester thereof, a benzyl ester thereof, a methoxyphenyl ester thereof or an indanyl ester thereof; R² represents a hydrogen atom, an isopentyl group, a benzyl group, a phenethyl group, a phenylpropyl group, a phenylbutyl group or a benzyloxy group; R³ represents an isobutyl group; R⁴ represents a biphenylyl group, a fluorobiphenylyl group, a methoxybiphenylyl group, a terphenylyl group, a naphthyl group or a methoxynaphthyl group; R⁵ represents a carboxyl group or a carboxyl group which is converted into a methyl ester thereof or a benzyl ester thereof; and A represents a methylene group.

8. The compound or a salt thereof as claimed in claim 2, wherein R⁴ represents a group represented by the formula [XI], [XII]or [XIII],

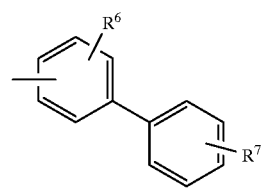

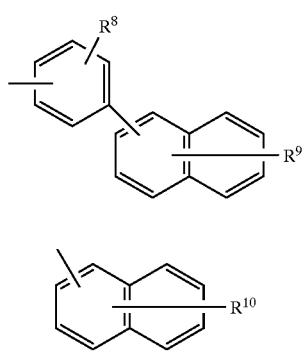

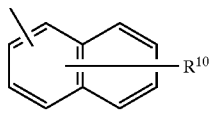

wherein
- $R^6$ represents a hydrogen atom or a nitro group;
- $R^7$ represents a hydrogen atom, a halogen atom, a lower alkyl group, a hydroxy group, a lower alkoxy group, a nitro group, an amino group or a phenyl group;
- $R^8$ and $R^9$ each represents a hydrogen atom; and
- $R^{10}$ represents a hydrogen atom, a halogen atom or a lower alkoxy group.

9. The compound or a salt thereof as claimed in claim 2, wherein $R^4$ represents a group represented by the formula [XI], [XII] or [XIII],

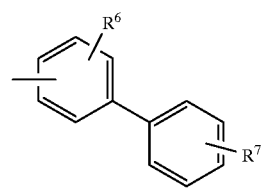

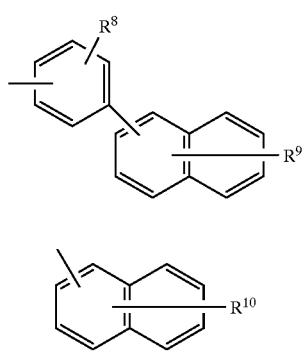

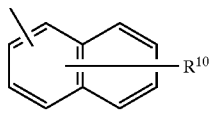

wherein
- $R^6$ represents a hydrogen atom or a nitro group;
- $R^7$ represents a hydrogen atom, a halogen atom, a lower alkyl group, a lower alkoxy group or a phenyl group;
- $R^8$ and $R^9$ each represents a hydrogen atom; and
- $R^{10}$ represents a hydrogen atom, a halogen atom or a lower alkoxy group.

10. The compound or a salt thereof as claimed in claim 2, wherein $R^4$ represents a biphenylyl group, a fluorobiphenylyl group, a chlorobiphenylyl group, a methylbiphenylyl group, a methoxybiphenylyl group, a nitrobiphenylyl group, a terphenylyl group, a naphthylphenyl group, a naphthyl group, a bromonaphthyl group or a methoxynaphthyl group.

11. The compound or a salt thereof as claimed in claim 2, wherein $R^4$ represents a group represented by the formula [XI] or [XIII],

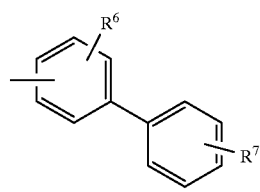

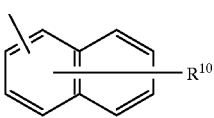

wherein
- $R^6$ represents a hydrogen atom;
- $R^7$ represents a hydrogen atom, a halogen atom, a lower alkoxy group or a phenyl group; and
- $R^{10}$ represents a hydrogen atom or a lower alkoxy group.

12. The compound or a salt thereof as claimed in claim 2, wherein $R^4$ represents a biphenylyl group, a fluorobiphenylyl group, a methoxybiphenylyl group, a terphenylyl group, a naphthyl group or a methoxynaphthyl group.

13. The compound or a salt thereof as claimed in claim 2, wherein $R^3$ represents a lower alkyl group or a phenyl lower alkyl group.

14. The compound or a salt thereof as claimed in claim 2, wherein $R^3$ represents an isobutyl group.

15. The compound or a salt thereof as claimed in claim 2, wherein $R^2$ represents a hydrogen atom, a lower alkyl group, a phenyl lower alkyl group, lower alkoxy group or phenyl lower alkoxy group.

16. The compound or a salt thereof as claimed in claim 2, wherein $R^2$ represents a hydrogen atom, an isopentyl group, a benzyl group, a phenethyl group, a phenylpropyl group, a phenylbutyl group or a benzyloxy group.

17. The compound or a salt thereof as claimed in claim 2, wherein $R^1$ represents a carboxyl group or a carboxyl group which is converted into a lower alkyl ester thereof, a lower alkanoylamino-lower alkyl ester thereof, a phenyl lower alkyl ester thereof, a lower alkoxyphenyl ester thereof, a lower alkanoylaminophenyl ester thereof or an indanyl ester thereof; a carboxyl group which is converted into an amide thereof with ammonia; a carboxyl group which is converted into a hydroxamic acid thereof; a phosphonic group or a phosphonic group which is converted into a lower alkyl ester thereof; and $R^5$ represents a carboxyl group or a carboxyl group which is converted into a lower alkyl ester thereof, a lower alkanoylamino-lower alkyl ester thereof, a phenyl lower alkyl ester thereof, a lower alkoxyphenyl ester thereof, a lower alkanoylaminophenyl ester thereof or an indanyl ester thereof; a carboxyl group which is converted into an amide thereof with ammonia; or a carboxyl group which is converted into a hydroxamic acid thereof.

18. The compound or a salt thereof as claimed in claim 2, wherein $R^1$ represents a carboxyl group or a carboxyl group which is converted into a lower alkyl ester thereof, a lower alkanoylamino-lower alkyl ester thereof, a phenyl lower alkyl ester thereof, a lower alkoxyphenyl ester thereof, a lower alkanoylaminophenyl ester thereof or an indanyl ester thereof; a carboxyl group which is converted into a hydroxamic acid thereof; a phosphonic group or a phosphonic group which is converted into a lower alkyl ester thereof; and $R^5$ represents a carboxyl group or a carboxyl group which is converted into a lower alkyl ester thereof, a phenyl lower alkyl ester thereof or a lower alkanoylaminophenyl ester thereof.

19. The compound or a salt thereof as claimed in claim 2, wherein $R^1$ represents a carboxyl group or a carboxyl group which is converted into an ethyl ester thereof, a butyl ester thereof, an isopropyl ester thereof, an isobutyl ester thereof, a tert.-butyl ester thereof, an acetamidoethyl ester thereof, a benzyl ester thereof, a methoxyphenyl ester thereof, an acetamidophenyl ester thereof or an indanyl ester thereof; a carboxyl group which is converted into a hydroxamic acid thereof; a phosphonic group or a phosphonic group which is converted into an ethyl ester thereof; and $R^5$ represents a carboxyl group or a carboxyl group which is converted into a methyl ester thereof, a benzyl ester thereof or an acetamidophenyl ester thereof.

20. The compound or a salt thereof as claimed in claim 2, wherein $R^1$ represents a carboxyl group or a carboxyl group which is converted into a lower alkyl ester thereof, a phenyl lower alkyl ester thereof, a lower alkoxyphenyl ester thereof or an indanyl ester thereof; and $R^5$ represents a carboxyl group or a carboxyl group which is converted into a lower alkyl ester thereof or a phenyl lower alkyl ester thereof.

21. The compound or a salt thereof as claimed in claim 2, wherein $R^1$ represents a carboxyl group or a carboxyl group which is converted into an ethyl ester thereof, a butyl ester thereof, an isopropyl ester thereof, an isobutyl ester thereof, a tert.-butyl ester thereof, a benzyl ester thereof, a methoxyphenyl ester thereof or an indanyl ester thereof; and $R^5$ represents a carboxyl group or a carboxyl group which is converted into a methyl ester thereof or a benzyl ester thereof.

22. The compound or a salt thereof as claimed in claim 2, wherein $R^3$ represents a lower alkyl group or a phenyl lower alkyl group, and $R^4$ represents a group represented by the formula [XI], [XII] or [XIII],

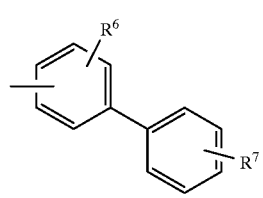
[XI]

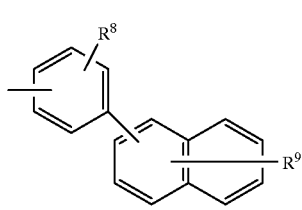
[XII]

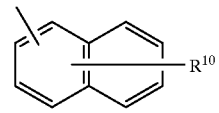
[XIII]

wherein $R^6$ represents a hydrogen atom or a nitro group;

$R^7$ represents a hydrogen atom, a halogen atom, a lower alkyl group, a hydroxy group, a lower alkoxy group, a nitro group, an amino group or a phenyl group;

$R^8$ and $R^9$ each represents a hydrogen atom; and $R^{10}$ represents a hydrogen atom, a halogen atom or a lower alkoxy group.

23. The compound or a salt thereof as claimed in claim 2, wherein $R^3$ represents a lower alkyl group, and $R^4$ represents a group represented by the formula [XI], [XII] or [XIII],

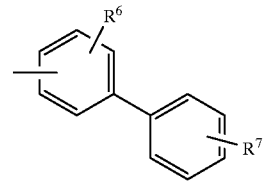
[XI]

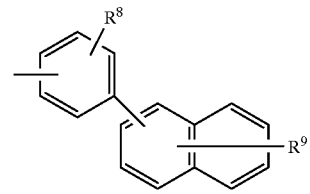
[XII]

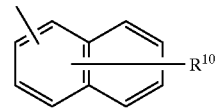
[XIII]

wherein $R^6$ represents a hydrogen atom or a nitro group;

$R^7$ represents a hydrogen atom, a halogen atom, a lower alkyl group, a lower alkoxy group or a phenyl group;

$R^8$ and $R^9$ each represents a hydrogen atom; and $R^{10}$ represents a hydrogen atom, a halogen atom or a lower alkoxy group.

24. The compound or a salt thereof as claimed in claim 2, wherein $R^3$ represents an isobutyl group, and $R^4$ represents a biphenylyl group, a fluorobiphenylyl group, a chlorobiphenylyl group, a methylbiphenylyl group, a methoxybiphenylyl group, a nitrobiphenylyl group, a terphenylyl group, a naphthylphenyl group, a naphthyl group, a bromonaphthyl group or a methoxynaphthyl group.

25. The compound or a salt thereof as claimed in claim 2, wherein $R^3$ represents a lower alkyl group, and $R^4$ represents a group represented by the formula [XI] or [XIII],

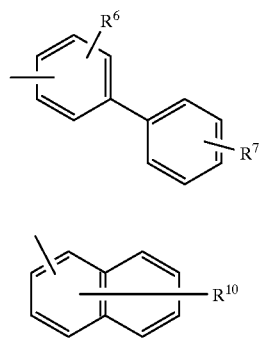

wherein

R⁶ represents a hydrogen atom;

R⁷ represents a hydrogen atom, a halogen atom, a lower alkoxy group or a phenyl group; and R¹⁰ represents a hydrogen atom or a lower alkoxy group.

26. The compound or a salt thereof as claimed in claim 2, wherein R³ represents an isobutyl group, and R⁴ represents a biphenylyl group, a fluorobiphenylyl group, a methoxybiphenylyl group, a terphenylyl group, a naphthyl group or a methoxynaphthyl group.

27. The compound or a salt thereof as claimed in claim 2, wherein R² represents a hydrogen atom, a lower alkyl group, a phenyl lower alkyl group, a lower alkoxy group or a phenyl lower alkoxy group, R³ represents a lower alkyl group or a phenyl lower alkyl group, and R⁴ represents a group represented by the formula [XI], [XII] or [XIII],

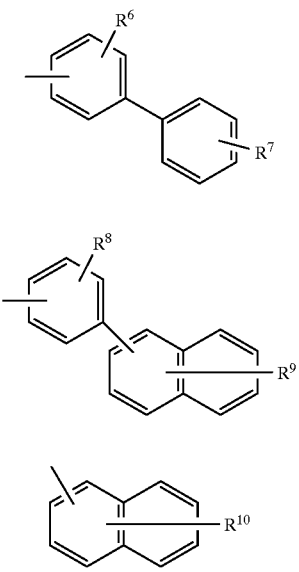

wherein

R⁶ represents a hydrogen atom or a nitro group;

R⁷ represents a hydrogen atom, a halogen atom, a lower alkyl group, a hydroxy group, a lower alkoxy group, a nitro group, an amino group or a phenyl group;

R⁸ and R⁹ each represents a hydrogen atom; and

R¹⁰ represents a hydrogen atom, a halogen atom or a lower alkoxy group.

28. The compound or a salt thereof as claimed in claim 2, wherein R² represents a hydrogen atom, a lower alkyl group, a phenyl lower alkyl group or a phenyl lower alkoxy group, R³ represents a lower alkyl group, and R⁴ represents a group represented by the formula [XI], [XII] or [XIII],

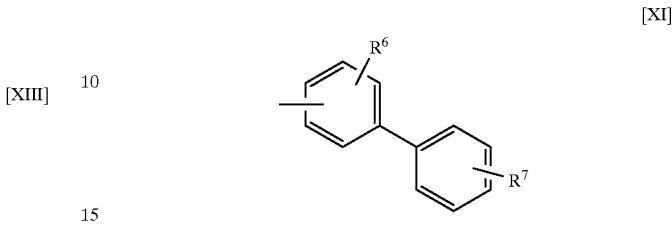

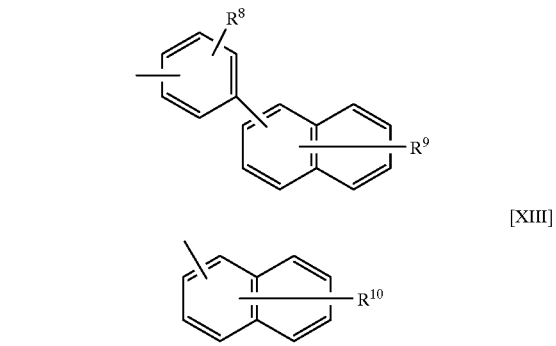

wherein

R⁶ represents a hydrogen atom or a nitro group;

R⁷ represents a hydrogen atom, a halogen atom, a lower alkyl group, a lower alkoxy group or a phenyl group;

R⁸ and R⁹ each represents a hydrogen atom; and

R¹⁰ represents a hydrogen atom, a halogen atom or a lower alkoxy group.

29. The compound or a salt thereof as claimed in claim 2, wherein R² represents a hydrogen atom, an isopentyl group, a benzyl group, a phenethyl group, a phenylpropyl group, a phenylbutyl group or a benzyloxy group, R³ represents an isobutyl group, and R⁴ represents a biphenylyl group, a fluorobiphenylyl group, a chlorobiphenylyl group, a methylbiphenylyl group, a methoxybiphenylyl group, a nitrobiphenylyl group, a terphenylyl group, a naphthylphenyl group, a naphthyl group, a bromonaphthyl group or a methoxy naphthyl group.

30. The compound or a salt thereof as claimed in claim 2, wherein R² represents a hydrogen atom, a lower alkyl group, a phenyl lower alkyl group or a phenyl lower alkoxy group, R³ represents a lower alkyl group, and R⁴ represents a group represented by the formula [XI] or [XIII],

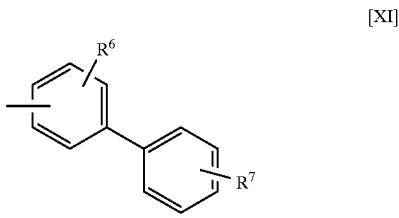

-continued

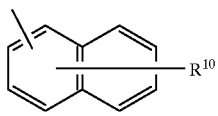

[XIII]

wherein
$R^6$ represents a hydrogen atom;
$R^7$ represents a hydrogen atom, a halogen atom, a lower alkoxy group or a phenyl group; and
$R^{10}$ represents a hydrogen atom or a lower alkoxy group.

31. The compound or a salt thereof as claimed in claim 2, wherein $R^2$ represents a hydrogen atom, an isopentyl group, a benzyl group, a phenethyl group, a phenylpropyl group, a phenylbutyl group or a benzyloxy group, $R^3$ represents an isobutyl group, and $R^4$ represents a biphenylyl group, a fluorobiphenylyl group, a methoxybiphenylyl group, a terphenylyl group, a naphthyl group or a methoxynaphthyl group.

32. 3-(4-Biphenylyl)-2-[3-(2-carboxyethyl)-3-isobutylureido]propionic acid or a salt thereof.

33. 3-(4-Biphenylyl)-2-[3-(2-carboxy-5-methylhexyl)-3-isobutylureido]propionic acid or a salt thereof.

34. 3-(4-Biphenylyl)-2-[3-(2-carboxy-4-phenylbutyl)-3-isobutylureido]propionic acid or a salt thereof.

35. 2-[3-(2-Benzyloxy-2-carboxyethyl)-3-isobutylureido]-3-(4-biphenylyl)propionic acid or a salt thereof.

36. 2-[3-(2-Carboxyethyl)-3-isobutylureido]-3-(2-naphthyl)propionic acid or a salt thereof.

37. 2-[3-(2-Carboxy-4-phenylbutyl)-3-isobutylureido]-3-(2-naphthyl)propionic acid or a salt thereof.

38. (2S)-3-(4-Biphenylyl)-2-[3-(2-carboxyethyl)-3-isobutylureido]propionic acid or a salt thereof.

39. (2S)-3-(4-Biphenylyl)-2-[3-(2-butoxycarbonylethyl)-3-isobutylureido]propionic acid or a salt thereof.

40. An endopeptidase 24.11 inhibitor comprising an effective endopeptidase 24.11 inhibiting amount of the compound or a salt thereof as claimed in claim 1 as an active ingredient in combination with a pharmaceutically acceptable carrier.

* * * * *